United States Patent [19]
Schmidhammer

[11] Patent Number: 6,136,817
[45] Date of Patent: *Oct. 24, 2000

[54] OPIOID RECEPTOR ANTAGONIST COMPOUNDS

[75] Inventor: Helmut Schmidhammer, Insbruck, Austria

[73] Assignee: Astra AB, Sweden

[*] Notice: This patent is subject to a terminal disclaimer.

[21] Appl. No.: 08/507,369

[22] PCT Filed: May 9, 1995

[86] PCT No.: PCT/SE95/00503

§ 371 Date: Aug. 22, 1995

§ 102(e) Date: Aug. 22, 1995

[87] PCT Pub. No.: WO95/31463

PCT Pub. Date: Nov. 23, 1995

[30] Foreign Application Priority Data

May 18, 1994 [SE] Sweden .................................. 9401728

[51] Int. Cl.[7] ...................... A61K 31/485; C07D 489/09; C07D 491/18
[52] U.S. Cl. .............................. 514/279; 546/35; 546/37; 546/44; 546/45
[58] Field of Search ......................... 546/35, 37; 514/279

[56] References Cited

U.S. PATENT DOCUMENTS

| | | | |
|---|---|---|---|
| 4,816,586 | 3/1989 | Portoghese | 544/340 |
| 5,223,507 | 6/1993 | Dappen et al. | 514/279 |
| 5,225,417 | 7/1993 | Dappen et al. | 514/279 |

FOREIGN PATENT DOCUMENTS

| | | |
|---|---|---|
| 0 456 833 | 11/1991 | European Pat. Off. . |
| 614 898 | 4/1994 | European Pat. Off. . |
| 4-342529 | 11/1992 | Japan . |
| WO 94/07896 | 4/1994 | WIPO . |

OTHER PUBLICATIONS

Portoghese, et al., "Design of Peptidomimetic δ Opioid Receptor Antagonists Using the Message–Address Concept," *J. Med. Chem. 33*:1714–1720 (1990).
Portoghese, et al., "Opioid Agonist and Antagonist Activities of Morphindoles Related to Naltrindole," *J. Med. Chem. 35*:4325–4329 (1992).
Dialog abstract of Japanese counterpart of WO94/07896 (listed above as document AL1), Derwent World Patents Index accession no. 94–135494/199416.
Dialog abstract of Japanese patent JP 4–3342529 (listed on p. 1 as document AN1), Derwent World Patents Index accession No. 93–14047/199302).
International Search Report for Swedish appl. 9401728–2 (priority appl. of PCT/SE95/00503).
Hiroshi et al., "Preparation of Naloxyindole Derivatives as δ–Opioid Antagonists," *Chemical Abstracts* 119:1096–1097, abstr. # 95503d (1993).
Portoghese et al., "Bimorphinans as Highly Selective, Potent κ Opioid Receptor Antagonists," *J. Med. Chem. 30*:238–239 (1987).
Portoghese et al., "Application of the Message–Address Concept in the Design of Highly Potent and Selective Non–Peptide δ Opioid Receptor Antagonists," *J. Med. Chem. 31*:281–282 (1988).
Portoghese, "An Approach to the Design of Receptor-Type--Selective Non-Peptide Antagonists of Peptidergic Receptors: δ Opioid Antagonists," *J. Med. Chem. 34*:1757–1762 (1991).
Schmidhammer et al., "Synthesis and Biological Evaluation of 14–Alkoxymorphinans. 2.[1] (–)-N-(Cyclopropylmethyl)-4, 14–dimethoxymorphinan-6-one, a Selective μ Opioid Receptor Antagonist," *J. Med. Chem. 32*:418–421 (1989).
Schmidhammer et al., "Synthesis and Biological Evaluation of 14–Alkoxymorphinans. 3.[1] Extensive Study on Cyprodime–Related Compounds," *J. Med. Chem. 33*:1200–1206 (1990).

*Primary Examiner*—Evelyn Mei Huang
*Attorney, Agent, or Firm*—Michael A. Sanzo; Vinson & Elkins L.L.P.

[57] ABSTRACT

New morphinane derivatives of the formula

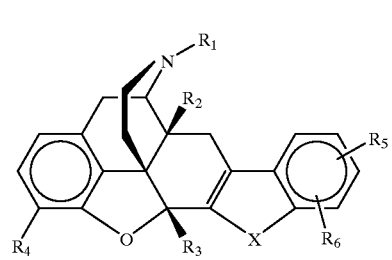

(I)

their pharmaceutically acceptable salts, a process for their preparation and their use in the manufacture of pharmaceutical preparations.

11 Claims, No Drawings

OPIOID RECEPTOR ANTAGONIST COMPOUNDS

CROSS REFERENCE TO RELATED APPLICATIONS

The present application claims priority to international application PCT/SE95/00503, filed on May 9, 1995, and also to Swedish application 9401728-2, filed on May 18, 1994.

FIELD OF THE INVENTION

The present invention is related to novel δ opioid receptor antagonists as well as to their pharmaceutically acceptable salts, a process for their preparation and their use in the manufacture of pharmaceutical preparations.

BACKGROUND OF THE INVENTION

Opiod antagonists have been indispensable as tools in opioid research. For example, the chief criterion for the classification of an agonist effect as being opioid receptor mediated is the ability of known opioid antagonists naloxone or naltrexone to reversibly antagonize this effect in a competitive fashion. The usefulness of naloxone and naltrexone for this purpose stems from the fact that they are universal opioid antagonists; that is, they are capable of antagonizing the agonist effects mediated by multiple opioid receptor types.

Since it is now firmly established that there are a minimum of three opioid receptor types ($\mu$, $\kappa$ and $\delta$), it has become increasingly evident that selective opioid antagonists are valuable pharmacological tools for identifying receptor types involved in the interaction with opioid agonists. One of the major advantages of selective opioid antagonists over selective agonists is their utility in probing the interaction of endogenous opioid peptides and new opioid agonists with opioid receptor types. Moreover, since it is sometimes not easy to distinguish among $\mu$, $\kappa$ and $\delta$ opioid receptor mediated agonist effects if the pharmacological endpoints are identical (e.g. antinociception or inhibition of a smooth muscle preparation by agonists), selective antagonists clearly have wider utility as tools than selective agonists.

The general utility of selective antagonists as pharmacological tools depends upon the correlation of in vitro and in vivo acitivity. This can be accomplished more easily with non-peptide ligands because they generally can penetrate the blood-brain barrier and therefore can be administered peripherally in vivo. Also, they are less subject to metabolism than are peptides.

In addition to their uses as pharmacological tools, selective, non-peptide opioid antagonists have been described as having potential clinical applications in the treatment of a variety of disorders where endogenous opioids play a modulatory role. These include for instance disorders of food intake, shock, constipation, mental disorders, CNS injury, alcoholism, and immune function (immune stimulation or suppression) (P. S. Portoghese et al., J. Med. Chem., Vol 34: 1757–1762, 1991).

Non-peptide, competitive, δ-selective opioid antagonists have been found recently. The prototypes are: cyprodime for $\mu$ (H. Schmidhammer et al., J. Med. Chem., Vol. 32:418–421, 1989; H. Schmidhammer et al., J. Med. Chem., Vol. 33: 1200–1206, 1990), norbinaltorphimine for $\kappa$ (P. S. Portoghese et al., J. Med. Chem., Vol. 30:238–239, 1987), and naltrindole for δ opioid receptors (P. S. Portoghese et al., J. Med. Chem., Vol. 31:281–282, 1988).

These compounds (cyprodime, norbinaltorphinine and naltrindole) are being used as pharmacological tools. They have been tritium labelled and can be used as receptor selective ligands in opioid receptor binding studies to sort out the affinities of new ligands to different receptors and to determine whether a compound is selective to a special receptor.

An object of the present invention was to find new, highly selective δ opioid receptor antagonists with high potency. Another object was to find highly selective δ opioid receptor antagonists with high immunosuppressive potency. The high selectivity for δ opioid receptors would repress adverse side effects caused by the interaction with other receptors. Still another object was to find compounds which have a brain-cell protecting effect. The problem with the δ opiod receptor antagonists known from the prior art is that they are not highly selective.

PRIOR ART

Certain opioid agonists represented by morphine, which act on $\mu$ receptors, are known to exhibit immunosuppressive effects. The agonist enkephalin, which acts on δ opioid receptors, exhibit immunostimulating effects (Plotnikoff, Enkephalins and Endorphins, Stress and Immune System, Plenum Press, 1986). Although a number of reports have been issued concerning the immunosuppressive effects of agonists of $\mu$ receptors, it is difficult to develop an immunosuppressive agent by employing an agonist of $\mu$ receptors, since such agonists show critical side effects such as addiction, respiratory depression, constipation etc.

Recently it has been reported that δ-selective opioid antagonists have immunosuppressive effects. See EP 456 833, EP 485 636 and EP 614 898.

OUTLINE OF THE INVENTION

The present invention provides novel compounds of the formula (I)

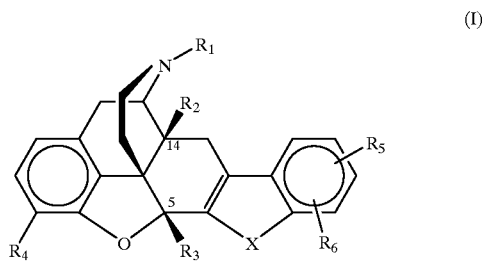

wherein

R$_1$ represents C$_1$–C$_{10}$ alkenyl; C$_4$–C$_{10}$ cycloalkylalkyl wherein the cycloalkyl is C$_3$–C$_6$ cycloalkyl and the alkyl is C$_1$–C$_4$ alkyl; C$_4$–C$_{10}$ cykloalkenylalkyl wherein the cycloalkenyl is C$_3$–C$_6$ cykloalkenyl and the alkyl is C$_1$–C$_4$ alkyl; C$_7$–C$_{16}$ arylalkyl wherein the aryl is C$_6$–C$_{10}$ aryl and the alkyl is C$_1$–C$_6$ alkyl; C$_8$–C$_{16}$ arylalkenyl wherein the aryl is C$_6$–C$_{10}$ aryl and the alkenyl is C$_2$–C$_6$ alkenyl;

R$_2$ represents hydrogen, hydroxy, C$_1$–C$_6$ alkoxy; C$_1$–C$_6$ alkenyloxy; C$_7$–C$_{16}$ arylalkyloxy wherein the aryl is C$_6$–C$_{10}$ aryl and the alkyloxy is C$_1$–C$_6$ alkyloxy; C$_7$–C$_{16}$ arylalkenyloxy wherein the aryl is C$_6$–C$_{10}$ aryl and the alkenyloxy is C$_1$–C$_6$ alkenyloxy; C$_1$–C$_6$ alkanoyloxy; C$_7$–C$_{16}$ arylalkanoyloxy wherein the aryl is C$_6$–C$_{10}$ aryl and the alkylaroyloxy is C$_1$–C$_6$ alkylaroyloxy;

R$_3$ represents hydrogen, C$_1$–C$_6$ alkyl; C$_1$–C$_6$ alkenyl; C$_7$–C$_{16}$ arylalkyl wherein the aryl is C$_6$–C$_{10}$ aryl and the alkyl is C$_1$–C$_6$ alkyl; C$_7$–C$_{16}$ arylalkenyl wherein the aryl is C$_6$–C$_{10}$ aryl and the alkenyl is C$_1$–C$_6$ alkenyl; hydroxy(C$_1$–C$_6$)alkyl; alkoxyalkyl wherein the alkoxy is C$_1$–C$_6$ alkoxy and the alkyl is C$_1$–C$_6$ alkyl; CO$_2$H; CO$_2$(C$_1$–C$_6$ alkyl);

R$_4$ is hydrogen, hydroxy; C$_1$–C$_6$ alkoxy; C$_7$–C$_{16}$ arylalkyloxy wherein the aryl is C$_6$–C$_{10}$ aryl and the alkyloxy is C$_1$–C$_6$ alkyloxy; C$_1$–C$_6$ alkenyloxy; C$_1$–C$_6$ alkanoyloxy; C$_7$–C$_{16}$ arylalkanoyloxy wherein the aryl is C$_6$–C$_{10}$ aryl and the alkanoyloxy is C$_1$–C$_6$ aLkanoyloxy; C$_2$–C$_{10}$ alkyloxyalkoxy wherein alkyloxy is C$_1$–C$_4$ alkyloxy and alkoxy is C$_1$–C$_6$ alkoxy;

R$_5$ and R$_6$ each independently represent hydrogen; OH; C$_1$–C$_6$ alkoxy; C$_1$–C$_6$ alkyl; hydroxyalkyl wherein the alkyl is C$_1$–C$_6$ alkyl; halo; nitro; cyano; thiocyanato; trifluoromethyl; CO$_2$H; CO$_2$(C$_1$–C$_6$ alkyl); CONH$_2$; CONH(C$_1$–C$_6$ alkyl); CON(C$_1$–C$_6$ alkyl)$_2$; amino; C$_1$–C$_6$ monoalkyl amino; C$_1$–C$_6$ dialkyl amino, C$_5$–C$_6$ cycloalkylamino; SH; SO$_3$H; SO$_3$(C$_1$–C$_6$ alkyl); SO$_2$(C$_1$–C$_6$ alkyl); SO$_2$NH$_2$; SO$_2$NH(C$_1$–C$_6$ alkyl); SO$_2$NH(C$_7$–C$_{16}$ arylalkyl); SO(C$_1$–C$_6$ alkyl); or R$_5$ and R$_6$ together form a phenyl ring which may be unsubstituted or substituted by halo, nitro, cyano, thiocyanato; C$_1$–C$_6$ alkyl; trifluoromethyl; C$_1$–C$_6$ alkoxy, CO$_2$H, CO(C$_1$–C$_6$ alkyl), amino, C$_1$–C$_6$ monoalkylamino, C$_1$–C$_6$ dialkylamino, SH; SO$_3$H; SO$_3$(C$_1$–C$_6$ alkyl), SO$_2$(C$_1$–C$_6$ alkyl), SO(C$_1$–C$_6$ alkyl), and X represents oxygen; sulfur; CH=CH or NR$^9$ wherein R$_9$ is H, C$_1$–C$_6$ alkyl, C$_1$–C$_6$ alkenyl, C$_7$–C$_{16}$ arylalkyl wherein the aryl is C$_6$–C$_{10}$ aryl and the alkyl is C$_1$–C$_6$ alkyl, C$_7$–C$_{16}$ arylalkenyl wherein the aryl is C$_6$–C$_{10}$ aryl and the alkenyl is C$_1$–C$_6$ alkenyl; C$_1$–C$_6$ alkanoyl, with the proviso that when R$_2$ is hydroxy R$_3$ cannot be hydrogen, except when R$_4$ is hydrogen, OCH$_2$OCH$_3$, OCH$_2$OC$_2$H$_5$ or OC(Ph)$_3$;

and pharmacologically acceptable salts thereof.

By aryl the following definitions are intended throughout the whole patent application.

Aryl may be unsubstituted or mono-, di- or trisubstituted independently with hydroxy, halo, nitro, cyano, thiocyanato, trifluoromethyl, C$_1$–C$_3$ alkyl, C$_1$–C$_3$ alkoxy, CO$_2$H, CO$_2$(C$_1$–C$_3$)alkyl, CONH$_2$, CONH(C$_1$–C$_3$ alkyl), CON(C$_1$–C$_3$ alkyl)$_2$, CO(C$_1$–C$_3$ alkyl), amino, (C$_1$–C$_3$ monoalkyl)amino, (C$_1$–C$_3$ dialkyl)armino, C$_5$–C$_6$ cycloalkylamino, (C$_1$–C$_3$ alkanoyl)amino, SH, SO$_3$H, SO$_3$ (C$_1$–C$_3$ alkyl), SO$_2$ (C$_1$–C$_3$ alkyl), SO(C$_1$–C$_3$ alkyl), C$_1$–C$_3$ alkylthio or C$_1$–C$_3$ alkanoylthio.

In a preferred embodiment

R$_1$ is selected from allyl, cinnamyl, cyclopropylmethyl or cyclobutylmethyl;

R$_2$ is selected from methoxy, ethoxy, n-propyloxy, benzyloxy, benzyloxy substituted in the aromatic ring with F, Cl, NO$_2$, CN, CF$_3$, CH$_3$ or OCH$_3$; allyloxy, cinnamyloxy or 3-phenylpropyloxy;

R$_3$ is selected from hydrogen, methyl, ethyl, benzyl or allyl;

R$_4$ is selected from hydroxy, methoxy, methoxymethoxy or acetyloxy;

R$_5$ and R$_6$ are each and independently selected from hydrogen, nitro, cyano, chloro, fluoro, bromo, trifluoromethyl; CO$_2$H; CO$_2$CH$_3$, CONH$_2$; CONH CH$_3$, CH$_3$, SH; SO$_2$NH$_2$; N(CH$_3$)$_2$, SO$_2$ CH$_3$; and X is selected from O, NH, N CH$_3$, N-benzyl, N-allyl.

In an especially preferred embodiment R$_1$ is allyl or cyclopropylmethyl;

R$_2$ is selected from methoxy, ethoxy, n-propyloxy, benzyloxy substituted in the aromatic ring with chlorine;

R$_3$ is selected from hydrogen or CH$_3$;

R$_4$ is hydroxy

R$_5$ and R$_6$ are each independently selected from hydrogen, CO$_2$H, CONH$_2$, SO$_2$NH$_2$ or SO$_2$CH$_3$; and X is selected from O or NH.

The best mode known at present is to use the compounds of Examples 1, 6, 8, 18, 24, 41 and 42.

The novel compounds according to the invention are useful as immunsuppressive agents and/or as analgesics, and also after CNS-injuries by exerting a brain-cell protecting effect.

Earlier studies (cf. page 3) accomplished with &-selective opioid antagonists have shown that this class of compounds exhibits immunosuppressive effects. Thus, the compounds of formula (I) of the present invention may be used for suppressing the rejection of transplants after organ transplantations and may be used in the treatment of rheumatic diseases, e.g. rheumatoid arthritis and/or as analgesics.

Pharmaceutically and pharmacologically acceptable salts of the compounds of formula I are also comprised in the invention. Suitable salts are inorganic salts such as HCl salt, HBr salt, sulfuric acid salt, phosphoric acid salt. Organic acid salts such as methanesulfonic acid salt, salicylc acid salt, fumaric acid salt, maleic acid salt, succinic acid salt, aspartic acid salt, citric acid salt, oxalic acid salt, orotic acid salt, although the salts are not restricted thereto, can also be used according to the invention.

PREPARATION

The compounds represented by formula (I) may be obtained by the following methods:

Thebaine of the formula

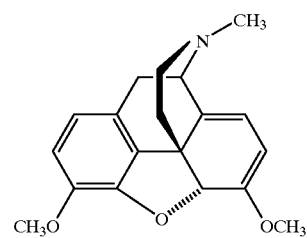

is being treated with dialkylsulfates, fluorosulfonic acid alkyl esters, alkylsulfonic acid alkyl esters, arylsulfonic acid alkylesters, alkyl halides, aralkyl halides, alkylsulfonic acid aralkyl esters, arylsulfonic acid aralkyl, arylalkenyl halides, chloroformates, in solvents such as tetrahydrofurane or diethyl ether using a strong base such as n-butyl lithium, lithium diethyl amide or lithium diisopropyl arnide at low temperatures (–20 to –80° C.) (s. Boden et al., J.org.Chem., Vol.47: 1347–1349, 1982; Schmidhammer et al., Helv.Chim.Acta, Vol.71:642–647, 1988), giving compounds of the formula II

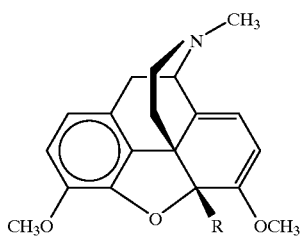

(II)

wherein
R is $C_1$–$C_6$ alkyl; $C_1$–$C_6$ alkenyl; $C_7$–$C_{16}$ aralkyl wherein the aryl is $C_6$–$C_{10}$ aryl and the alkyl is $C_1$–$C_6$ alkyl; $C_7$–$C_{16}$ arylalkenyl wherein the aryl is $C_6$–$C_{10}$ aryl and the alkenyl is $C_1$–$C_6$ alkenyl; alkoxyalkyl wherein the alkoxy is $C_1$–$C_6$ alkoxy and the alkyl is $C_1$–$C_6$ alkyl; $CO_2$ ($C_1$–$C_6$ alkyl); The substituted thebaine derivatives (formula (II)) or thebaine are converted into the corresponding 14-hydroxycodeinones according to formula III

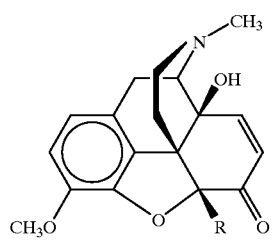

(III)

wherein
R is as defined above or being hydrogen,
by reaction with performic acid (s. Schmidhammer et al., Helv.Chim.Acta, Vol. 71:1801–1804, 1988) or m-chloroperbenzoic acid at a temperature between 0 and 60° C. The preferred procedure is the reaction with performic acid at 0–10° C. (H. Schmidhammer et al., Helv.Chim.Acta, Vol. 71:1801–1804, 1988). These 14-hydroxycodeinones being treated with dialkyl sulfates, alkyl halides, alkenyl halides, aralkyl halides, arylalkenyl halides, chloroformates, in solvents such as N,N-dimethyl formamide or tetrahydrofurane using a strong base such as sodium hydride, potassium hydride or sodium amide giving compounds of formula (IV),

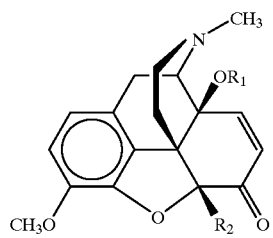

(IV)

wherein
$R_1$ is $C_1$–$C_6$ alkyl, $C_1$–$C_6$ alkenyl, $C_7$–$C_{16}$ arylalkyl wherein the aryl is $C_6$–$C_{10}$ aryl and the alkyl is $C_1$–$C_6$ alkyl, $C_7$–$C_{16}$ arylalkenyl wherein the aryl is $C_6$–$C_{10}$ aryl and the alkenyl is $C_1$–$C_6$ alkenyl, $C_1$–$C_6$ alkanoyl, $C_7$–$C_{20}$ arylalkanoyl wherein the aryl is $C_6$–$C_{14}$ aryl and the alkyl is $C_1$–$C_6$ alkyl, $C_7$–$C_{20}$ arylalkenoyl wherein the aryl is $C_6$–$C_{14}$ aryl and the alkyl is $C_1$–$C_6$ alkenoyl;

$R_2$ is hydrogen; $C_1$–$C_6$ alkyl; $C_1$–$C_6$ alkenyl $C_7$–$C_{16}$ arylalkyl wherein the aryl is $C_6$–$C_{10}$ aryl and the alkyl is $C_1$–$C_6$ alkyl; $C_7$–$C_{16}$ arylalkenyl wherein the aryl is $C_6$–$C_{10}$ aryl and the alkenyl is $C_1$–$C_6$ alkenyl; alkoxyalkyl wherein the alkoxy is $C_1$–$C_6$ alkoxy and the alkyl is $C_1$–$C_6$ alkyl; $CO_2$($C_1$–$C_6$ alkyl);

which in turn are reduced by catalytic hydrogenation using a catlayst such as palladium on charcoal and solvents such as methanol, ethanol or glacial acetic acid to give compounds of formula (V)

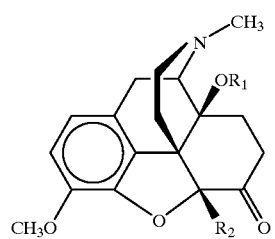

(V)

wherein
$R_1$ is $C_1$–$C_6$ alkyl, $C_7$–$C_{16}$ arylalkyl wherein the aryl is $C_6$–$C_{10}$ aryl and the alkyl is $C_1$–$C_6$ alkyl, $C_1$–$C_6$ alkanoyl, $C_7$–$C_{16}$ arylalkanoyl wherein the aryl is $C_6$–$C_{10}$ aryl and the alkanoyl is $C_1$–$C_6$ alkanoyl; and $R_2$ is hydrogen; $C_1$–$C_6$ alkyl, $C_1$–$C_6$ alkenyl $C_7$–$C_{16}$ arylalkyl wherein the aryl $C_6$–$C_{10}$ aryl and the alkyl is $C_1$–$C_6$ alkyl; $C_7$–$C_{16}$ arylalkenyl wherein the aryl is $C_6$–$C_{10}$ aryl and alkenyl is $C_1$–$C_6$ alkenyl; alkoxyalkyl wherein the alkoxy is $C_1$–$C_6$ alkyl; $CO_2$($C_1$–$C_6$ alkyl);

Thereafter N-demethylation can be carried out using chloroformates or cyanogen bromide to give intermediates of formula (VI)

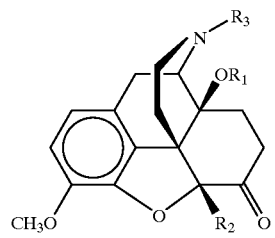

(VI)

wherein
$R_1$ and $R_2$ are as defined above in formula (IV); and
$R_3$ is $CO_2CHClCH_3$, $CO_2CH=CH_2$, $CO_2CH_2CCl_3$, $CO_2CH_2CH_3$, $CO_2Ph$, CN or the like.

The intermediate carbamates of formula (VI) can be cleaved by refluxing in alcohols (in the case of 1-chloroethyl carbamates), by addition of hydrogen halides or halogen and subsequent refluxing in alcohols (in the case of vinyl carbamates), or by reductive cleavage using zinc in glacial acetic acid or methanol (in the case of 2,2,2-trichloroethyl carbamates). Other carbonates may be cleaved using aqueous acid, alkali or hydrazine. The intermediate cyanamiides of formula (VI) can be deaved by acid hydrolysis. Alkylation of the corresponding N-nor derivatives of formula (VII)

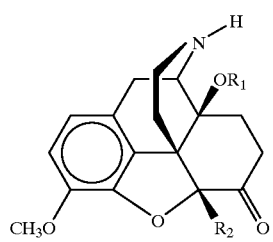

(VII)

wherein $R_1$ and $R_2$ are as defined above in formula (V), can be accomplished with alkenyl halides, cydoalkylalkyl halides, cycloalkenylalkyl halides, aralkyl halides, arylalkenyl halides, in solvents such as dichloromethane, chloroform, or N,N-dimethyl formamide in the presence of a base such as sodium hydrogen carbonate or potassium carbonate to yield derivatives of formula (VIII)

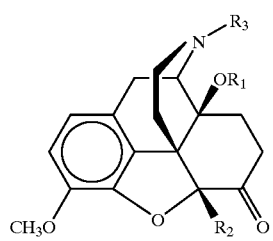

(VIII)

wherein $R_1$ and $R_2$ are as defined above in formula (V); and $R_3$ represents $C_1$–$C_6$ alkenyl; $C_7$–$C_{16}$ arylalkyl wherein the aryl is $C_6$–$C_{10}$ aryl and the alkyl is $C_1$–$C_6$ alkyl; $C_7$–$C_{16}$ arylalkenyl wherein the aryl is $C_6$–$C_{10}$ aryl and the alkenyl is $C_1$–$C_6$ alkenyl; $C_4$–$C_{10}$ cycloalkylalkyl wherein the cycloalkyl is $C_{3-C6}$ cydoalkyl and the alkyl is $C_1$–$C_4$ alkyl; $C_4$–$C_{10}$ cycloalkylalkenyl wherein the cydoalkenyl is $C_3$–$C_6$ cycloalkenyl and the alkyl is $C_1$–$C_4$ alkyl;

Ether cleavage can be carried out using boron tribromide (in a solvent such as dichloromethane or chloroform at about 0° C.), 48% hydrobromic acid (reflux), or other well known reagents for ether cleavage. The resulting phenols of formula (IX)

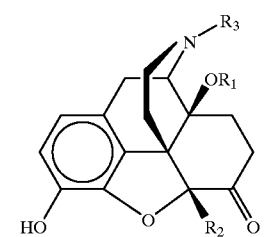

(IX)

wherein $R_1$, $R_2$ and $R_3$ are as defined above, are being alkylated using alkyl halides, alkyl sulfates, sulfonic acid esters, aralkyl halides, arylalkenyl halides or acylated using carbonic acid chlorides, or carbonic add esters to yield compounds of formula (X)

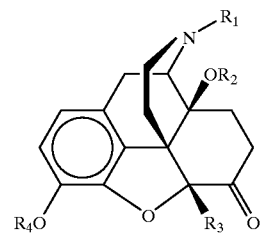

(X)

wherein $R_1$, $R_2$ and $R_3$ are as defined above; and $R_4$ is hydrogen, $C_1$–$C_6$ alkyl, $C_7$–$C_{16}$ arylalkyl wherein the aryl is $C_6$–$C_{10}$ aryl and the alkyl is $C_1$–$C_6$ alkyl, $C_1$–$C_6$ alkenyl, $C_7$–$C_{16}$ arylalkenyl wherein the aryl is $C_6$–$C_{10}$ aryl and the alkenyl is $C_1$–$C_6$ alkenyl; $C_1$–$C_6$ alkanoyl, $C_7$–$C_{16}$ arylalkanoyl wherein the aryl is $C_6$–$C_{10}$ aryl and the alkanoyl is $C_1$–$C_6$ alkanoyl, $C_2$–$C_{10}$ alkyloxyalkyl wherein alkyloxy is $C_1$–$C_4$ alkyloxy and alkyl is $C_1$–$C_6$ alkyl, Compounds of the formula (I) wherein $R_2$ is hydroxy may be obtained from compounds of formula (III) wherein R is defined as above. These compounds may be reduced by catalytic hydrogenation using a catalyst such as palladium on charcoal and solvents such as methanol, ethanol, or glacial acetic acid to give compounds of the formula (V) wherein $R_1$ is hydrogen and $R_2$ is defined for R in formula (II).

The following reaction sequence and procedures leading to compounds of formulas (VI), (VII), (VIII), (IX) and (X) wherein the substituent in position 14 is hydroxy and the other substitutents are defined as above, is analogous to the reaction sequence and procedures described above. Further conversion to compounds of the formula (I) wherein $R_2$ is hydroxy is described below.

Compounds of the formula (I) wherein $R_2$ is hydrogen may be obtained from compounds of the formula (II) wherein R is as defined above or hydrogen. Catalytic hydrogenation followed by acid hydrolysis (s. Boden et al., J. Org. Chem. Vol. 47:1347–1349, 1982) may provide compounds of formula (XI)

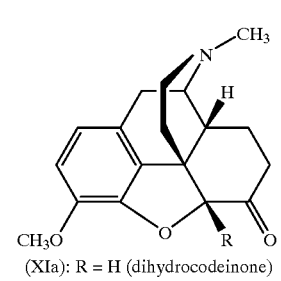

(XI)

(XIa): R = H (dihydrocodeinone)

wherein R is as defined above in formula (II) or hydrogen.

Compounds of the formula (XI) and (XIa) (Mannich and Lowenheim, Arch.Pharm.Vol. 258:295, 1920) can be converted into compounds of formulas (V), (VI), (VII), (VIII), (IX), and (X) wherein the substituent in position 14 is hydrogen and $R_2$ and $R_3$ are as defined above, similarly as outlined above. Further conversion into compounds of the formula (I) wherein $R_2$ is hydrogen is described below.

Compounds of the formula (I) wherein $R_4$ is hydrogen may be prepared from compounds of the formula (IX) by alkylation with 5-chloro-1-phenyl-$^1$H-tetrazole to give the corresponding phenyltetrazolyl ethers of the formula XII)

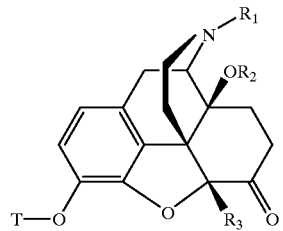

(XII)

wherein $R_1$, $R_2$ and $R_3$ are as defined above and $R_1$ also can be $CH_3$, and T is phenyltetrazolyl.

Catalytic hydrogenation may afford (H. Schmidhammer et al., J. Med. Chem. Vol. 27:1575–1579, 1984) compounds of the formula (XIII)

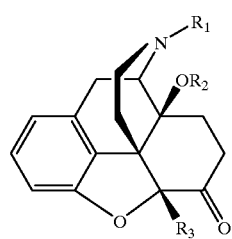

(XIII)

wherein $R_1$, $R_2$ and $R_3$ are as defined above and $R_1$ also can be $CH_3$;

In the case $R_1$ is $CH_3$, the N-methyl group has to be removed and the nitrogen alkylated as described above.

Alternatively, compounds of formula (I) wherein $R_1$ represents allyl or cyclopropylmethyl and $R_3$ represents H can be obtained by a shorter route starting either from naloxone (XIVa) or naltrexone (XIVa).

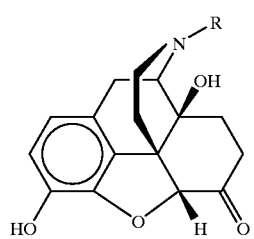

(XIV)

(XIVa): Naloxone—R is allyl (XIVb): Naltrexone—R is cyclopropylmethyl.

The 3-hydroxy group of compounds of formula (XIV) is being protected by alkylation with benzyl bromide, methoxymethyl bromide, ethoxymethyl bromide or trityl chloride (triphenylmethyl chloride) in a solvent such as N,N-dimethyl formamide or dichloromethane in the presence of a base to yield compounds of formula (XV)

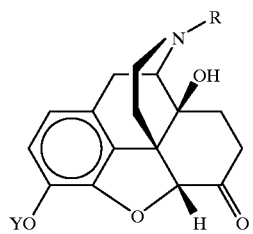

(XV)

wherein
R is allyl or cyclopropylmethyl and $Y=CH_2Ph$, $CH_2OCH_3$, $CH_2OC_2H_5$ or $C(Ph)_3$.

These compounds are alkylated, alkenylated, cycloalkylalkylated, arylalkylated or arylalkenylated with dialkyl sulfates, alkyl halides, alkenyl halides, arylalkyl halides or arylalkenyl halides in solvents such as N,N-dimethyl formamide or tetrahydrofurane using a strong base such as sodium hydride, potassium hydride or sodium amide. The resulting 6-0,14-0-dialkylated compounds of formula (XVI)

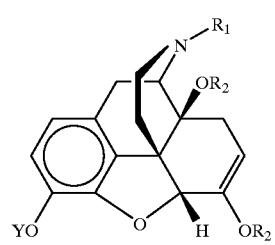

(XVI)

wherein
$R_1$ is allyl or cyclopropylmethyl; and
$R_2$ is $C_1$–$C_6$ alkyl, $C_1$–$C_6$ alkenyl, $C_7$–$C_{16}$ arylalkyl wherein the aryl is $C_6$–$C_{10}$ and the alkyl is $C_1$–$C_6$ alkoxy, $C_7$–$C_{16}$ arylalkenyl wherein the aryl is $C_6$–$C_{10}$ aryl and alkenyl is $C_1$–$C_6$ alkenyl; and Y as defined above;
can be hydrolized with diluted acids like hydrochloric acid or sulfuric acid to afford compounds or formula (XVII)

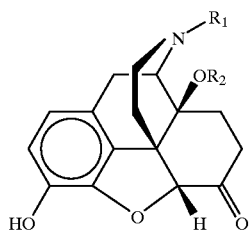

(XVII)

wherein
$R_1$ is allyl or cyclopropylmehtyl; and
$R_2$ is as defined above (formula XVI).

In the case $R_2$ is alkenyl or arylalkenyl the double bond may be reduced by catalytic hydrogenation to afford the corresponding saturated derivatives. Further conversion into compounds of formula (I) is described below.

Alternatively, compounds of formula (I) wherein $R_1$ represents allyl or cydopropylmethyl and $R_3$ represents H can be prepared also via the following route: The carbonyl group in position 6 of naloxone (XVa) and naltrexone (XVb), respectively, is being protected by reaction with ethylene glycol in the presence of an acid (e.g. methanesulfonic acid) at temperatures between 20 and 200° C. to give ketals of formula (XVIII)

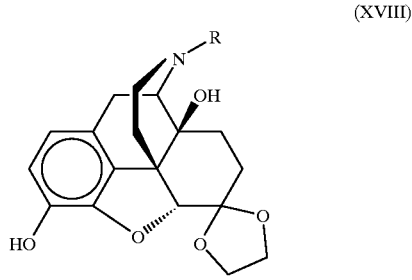

(XVIII)

wherein R is allyl or cydopropylmethyl.

The 3-hydroxy group of these ketals is being protected by alkylation with benzyl bromide, methoxymethyl bromide, ethoxymethyl bromide or trityl chloride in a solvent such as N,N-dimethyl formamide or dichloromethane in the presence of a base to yield compounds of formula (XIX)

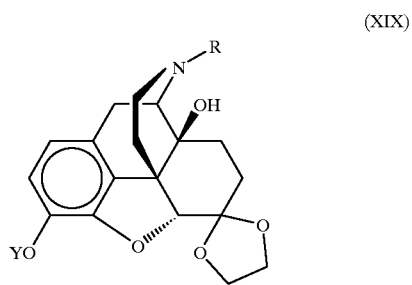

(XIX)

wherein R is allyl or cyclopropylmethyl and Y is as defined above.

These compounds are alkylated, alkenylated, arylalkylated or arylalkenylated with dialkyl suflates, alkyl halides, alkenyl halides, arylalkyl halides or arylalkenyl halides in solvents such as N,N-dimethyl formarnide or tetrahydrofurane using a strong base such as sodium hydride, potassium hydride or sodium amide. The resulting compounds of formula (XX)

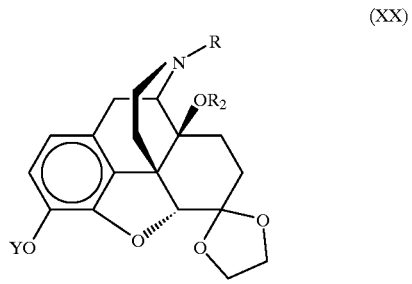

(XX)

wherein $R_1$ is allyl or cyclopropylmethyl, $R_2$ is as defined above (formula (XVI)) and Y is as defined above can be hydrolized in diluted acids like hydrochloride acid or sulfuric acid (a typical mixture for hydrolysis is: concentrated HCl: MeOH: $H_2O$ 3/6/1 v/v/v) to afford compounds of formula (XVII). Compounds of formula (I) wherein $R_1$ represents allyl or cyclopropyl-ethyl, $R_3$ represents H, and X represents NH or O can be prepared from compounds of formula (XVII) as described below.

Compounds of the formula (I) wherein $R_3$ is as defined above and X represents NH are obtained by reaction of compounds of formula (VIII), (X) or (XIII) with phenylhydrazine or substituted phenylhydrazine in solvents such as methanol, ethanol or glacial acetic acid in the presence of methanesulfonic acid, HCl or HBr. Phenylhydrazine substituted at the aromatic ring with hydroxy, halogen, $C_1$–$C_6$ alkyl, $C_1$–$C_6$ alkoxy, amino, nitro, cyano, thiocyanato, trifluoromethyl, $CO_2H$, $CO_2$ ($C_1$–$C_6$) alkyl, $CONH_2$, CONH ($C_1$–$C_6$ alkyl), $CON(C_1$–$C_6$alkyl$)_2$, $SO_2NH_2$, $SO_2$ ($C_1$–$C_6$) alkyl or the like may be employed. The reaction may be carried out at a temperature between 20 and 160° C., preferably between 20 and 80° C.

Compounds of formula (I) wherein $R_3$ is as defined above and X represents O are obtained by reaction of compounds of formula (VIII), (IX), (X) or (XIII) with O-phenylhydroxyl amine or substituted (at the aromatic ring) O-phenylhydroxyl-amine in solvents such as methanol ethanol, or glacial acetic acid in the presence of methanesulfonic acid, HCl or HBr. O-phenylhydroxylamine substituted at the aromatic ring with hydroxy, halogen, $C_1$–$C_6$ alkyl, $C_1$–$C_6$ alkoxy, amino, nitro, cyano, thiocyanato, trifluoromethyl, $CO_2H$, $CO_2$ ($C_1$–$C_6$) alkyl, $CONH_2$, CONH ($C_1$–$C_6$ alkyl), $CON(C_1$–$C_6$ alkyl$)_2$, $SO_2NH_2$, $SO_2$ ($C_1$–$C_6$) alkyl or the like may be employed.

The invention will now be described in more detail by the following examples which are not to be construed as limiting the invention.

EXAMPLES

Example 1

Synthesis of 17-(Cyclopropylmethyl)-6,7-dehydro-4,5α-epoxy-14-ethoxy-3-hydroxy-5-methyl-6,7-2',3'-indolomorphinan hydrochloride (compound 1).

A mixture of 14-O-ethyl-5-methylnaltrexone (H. Schmidhammer et al, Helv. Chim. Acta, Vol. 76: 476–480, 1993) (580 mg, 1.51 mmol), phenylhydrazine hydrochloride (394 mg, 2.72 mmol), and 7 ml of glacial acetic acid was refluxed for 23 h. After cooling, the reaction mixture was poured on ice, alkalized with conc. $NH_4OH$ and extracted with $CH_2Cl_2$ (3×30 ml). The combined organic layers were washed with $H_2O$(3×80 ml), dried over $Na_2SO_4$ and evaporated. The remaining residue (615 mg brownish foam) was dissolved in little MeOH and $Et_2O$/HCl was added. Thus, 550 mg (95%) of the compound 1 were isolated. For analysis a small amount was recrystallized from MeOH. m.p.>260° C. (dec.) IR (KBr): 3200 ($^+$NH, NH, OH)cm$^{-1}$. CI-MS: m/z 457 (M$^+$+1). $^1$H-NMR ((d$_6$)DMSO): δ 11.34, 9.21. and 8.55 (3 s, $^+$NH, NH, OH), 7.32 (m, 2 arom. H), 7.08 (t, J=8.1 Hz, 1 arom. H), 6.94 (t, J=8.1 Hz, 1 arom. H), 6.62 (d, J=8.1 Hz, 1 arom. H); 6.55 (d. J=8.1 Hz, 1 arom. H), 1.86 (s, $CH_3$—C(5)), 1.01 (t, J=6.8 Hz, 3H, $CH_3CH_2O$). Analysis calculated for $C_{29}H_{32}N_2O_3$·HCl·$H_2O$ (511.06): C 68.16, H 6.90, N 5.48, Cl 6.94; found: C 67.87, H 6.88, N 5.30, Cl 7.28.

Example 2

Synthesis of 17-Allyl-6,7-dihydro-4,5α-epoxy-14-ethoxy-3-hydroxy-5-methyl-6,7-2',3'-indolomorphinan hydrochloride (compound 2).

A mixture of 14-O-ethyl-5-methylnaloxone (H. Schntidhammer et al., Helv. Chim. Acta Vol. 76:476–480, 1993) (1.2 g, 2.66 mmol), phenylhydrazine hydrochloride (577 mg, 3.99 mmol), and 15 ml of glacial acetic acid was refluxed for 24 h. After cooling, the reaction mixture was poured on ice, alkalized with conc. NH$_4$OH and extracted with CH$_2$Cl$_2$ (3×80 ml), 1×30 ml). The combined organic layers were washed with H$_2$O (3×80 ml, 1×30 ml), dried over Na$_2$SO$_4$ and evaporated. The residue (1.3 g yellow-brown foam) was purified with column chromatography (alumina basic grade IV, elution with CH$_2$Cl$_2$). The corresponding fractions were combined and evaporated to give a colorless oil which was converted into the hydrochloride salt in the usual way and crystallized from MeOH/diethyl ether to yield 200 mg (17%) of the title compound 2. M.p. 168–170° C. IR (KBr):3200($^+$NH,OH)cm$^{-1}$. CI-MS: M/z 443 (M$^+$+1). $^1$H-NMR (CD$_3$OD): δ 7.39 (dd, J=7.8, 7.8 HZ, 2 arom. H), 7.14 (t, J=7.8 hz, 1 arom.H), 7.01 (t=7.8 HZ, 1 arom. H), 6.67 (s,2 arom. H), 6.02 (m, 1 olef. H), 5.72 (m, 2 olef. H), 1.99 (s, CH$_3$—C(5)), 1.09 (t, J=6.8 Hz, CH$_3$). Analysis calculated for C$_{28}$H$_{30}$N$_2$O$_3$. HCl. 1.5 H$_2$O (506.05): C 66.46, H 6.77 N 5.54, Cl 7.01; found: C 66.55, 6.68, N 5.39, Cl 6.98.

Example 3

Synthesis of 6,7-Dehydro-4,5α-epoxy-14-ethoxy-3-hydroxy-5-methyl-17-(2-phenyl)ethyl-6,7-2',3'-indolomorphinan hydrochloride (compound 5).

A mixture of 4,5α-epoxy-14-ethoxy-3-methoxy-5-methylmorphinan-6-one hydrochloride (H. Schmidhammer et al., Helv. Chim. Acta Vol. 76, 476–480,1993) (3.0 g, 7.88 mmol), potassium carbonate (3.9 g, 28.2 mmol), 2-phenylethyl bromide (1.41 ml, 10.4 mmol), and of 20 ml anhydrous NN-dimethyl formamide was stirred at 80° C. (bath temperature) for 2h. After cooling and addition of 130 ml of H$_2$O, the mixture was extracted with diethyl ether (3×60 ml). The combined organic layers were washed with H$_2$O(3×70 ml), dried over Na$_2$SO$_4$ and evaporated. The residue (3.6 yellow oil) was crystallized from MeOH to afford 2.1 g (70%) of 4,5α-epoxy-14-ethoxy-3-methoxy-5-methyl-17-(2-phenyl)ethylmorphinan-6-one (compound 3). M.p. 86–89° C. IR (KBr): 1725 (CO) cm$^{-1}$. CI-MS: m/z 448 (M$^+$+1). $^1$H-NMR (CDCl$_3$): δ 7.21 (m, 5 arom. H), 6.64 (d,J=8.2 Hz, 1 arom. H, 6.54 (d, J=8.2 Hz, 1 arom. H.), 3.85 (s, OCH$_3$), 1.60 (s, CH$_3$—C(5)), 1.12 (t, J=6.8 Hz, CH$_3$). Analysis calculated for C$_{28}$H$_{33}$NO$_4$ (447.55): C 75.14, H 7.43, N 3.13; found: C 75.04, H 7.69, N 3.26.

A solution of the compound 3 (1.5 g, 3.35 mmol) in 5 ml of 48% HBr was refluxed for 30 min and then evaporated. The residue was dissolved in MeOH and again evaporated (this procedure was repeated twice) to give a grey crystalline residue (1.7 g) which was treated with hot MeOH to yield 950 mg (63%) of the compound 4. M.p.>270° C. IR (KBr): 1720 (CO) cm$^{-1}$. CI-MS: m/z 434 (M$^+$+1). $^1$H-NMR (DMSO-d$_6$): δ 9.38 and 8.48 (2 s, $^+$NH, OH), 7.33 (m,5 arom. H), 6.68 (d, J=8.2 Hz, 1 arom. H), 6.64 (d, J=8.2 Hz, 1 arom. H), 1.51 (s, CH$_3$—C(5)), 1.34 (t, J=6.8 Hz, CH$_3$).

Analysis calculated for C$_{27}$H$_{31}$NO$_4$. HBr (514.45):C 63.04, H 6.27, N 2.72, Br 15.53; found: C 63.15, H 6.48, N 2.61, Br 15.37.

A mixture of the compound 4 (700 mg, 1.61 mmol), phenylhydrazine hydrochloride (513 mg), 3.54 mmol), and 15 ml of glacial acetic acid was refluxed for 6 h. The reaction mixture was poured on ice, alkalized with conc. NH$_4$OH and extracted with CH$_2$Cl$_2$ (3×80 ml, 1×30 ml). The combined organic layers were washed with H$_2$O(3×80 ml), dried over Na$_2$SO$_4$ and evaporated. The residue (600 mg slightly brown foam) was converted into the hydrochloride salt in the usual way and crystallized from MeOH/diethyl ether to yield 360 mg (51%) of the title compound 5 as slightly pink crystals. M.p.>225° C. IR (KBr):3400 and 3200 ($^+$NH, NH,OH). CI-MS: m/z 507 (M$^+$+1). $^1$H-NMR (DMSO-d$_6$): δ 11.34, 9.19 and 8.97 ($^+$NH, NH, OH), 7.34 (m, 7 arom. H), 7.08 (t, J=7.9 Hz, 1 arom.), 6.94 (t, J=7,9 Hz, 1 arom. H), 6.62 (d, J=8.4 Hz, 1 arom. H), 6.57 (d, J=8.4 Hz, 1 arom. H), 1.87 (s, CH3—C(5)),0.96 (t, J=6.9 Hz, CH$_3$). Analysis calculated for C$_{33}$H$_{34}$N$_2$O$_3$. HCl.2 H$_2$O (579.14): C 68.44, H 6.79, N 4.84, Cl 6.12; found: C 68.81, H 6.55, N 4.72, Cl 6.40.

Example 4

Synthesis of 17-Allyl-6,7-dehydro-4,5α-epoxy-3-hydroxy-14-methoxy-5-methyl-6,7-2',3'-indolomorphinan hydrochloride (compound 6).

A mixture of 14-O-methyl-5-methylnaloxone (H. Schmidhammer et al., Helv. Chim. Acta Vol. 77:1585–1589, 1994) (1.0 g, 2.8 mmol), phenylhydrazine hydrochloride (728 mg, 5.04 mmol), and 15 ml of glacial acetic acid was refluxed for 24 h. After cooling, the reaction mixture was poured on ice, alkalized with conc. NH$_4$OH and extracted with CH$_2$Cl$_2$ (3×80 ml, 1×30 ml). The combined organic layers were washed with H$_2$O (3×80 ml), dried over Na$_2$SO$_4$ and evaporated. The residue (1.1 g brownish foam) was converted in the usual way into the hydrochloride salt and crystallized from acetone to yield 190 mg (19%) of the title compound 6 as slightly brown crystals. M.p.>280° C. IR (KBr): 3200 ($^+$NH, NH,OH), $^1$H-NMR: δ 7.32 (dd, J=7.9, 7.9 Hz, 2 arom. H), 7.06 (t, J=7.9 Hz, 1 arom. H), 6.93 (t,=7.9 Hz, 1 arom. H), 6,63 (d, J=8.2 Hz, 1 arom. H), 6.55 (d, J=8.2 Hz, 1 arom. H), 6.02 (m, 1olef.H), 5.63 (m, 1 olef. H), 3.15 (s, OCH$_3$), 2.07 (s, CH$_3$—C(5)). Analysis calculated for C$_{27}$H$_{28}$N$_2$O$_3$. HCl. 1.7 H$_2$O. 0.9 MeOH (524.44): C64.41, H 7.09, N 5.22; found: C 64.44, H 6.87, N 4.94.

Example 5

Synthesis of 6,7-Dehydro-4,5ac-epoxy-3-hydroxy-14-methoxy-5-methyl-17-(2-phenyl)ethyl-6,7-2',3'-indolomorphinan Hydrochloride (compound 9).

A mixture of 4,5α-epoxy-3,14-dimethoxy-5-methylmorphinan-6-one hydrochloride (H. Schmidhammer et al., Helv. Chim. Acta Vol. 77:1585–1589, 1994) (2.24 g, 6.12 mmol), potassium carbonate (3.0 g, 21.9 mmol), 2-phenylethyl bromide (1.05 ml, 7.74 mmol), and 15 ml of anhydrous N,N-dimethyl formamide was stirred at 80° C. (bath temperature) for 2 h. After cooling and addition of 110 ml of H$_2$O, the mixture was extracted with diethyl ether (3×60 ml). The combined organic layers were washed with H$_2$O(3×70 ml), dried over Na$_2$SO$_4$ and evaporated. The residue (2.9 yellow oil) was converted into the hydrobromide salt in the usual way and crystallized from MeOH to give 1.4 g (63%) of 4,5α-epoxy-3,14-dimethoxy-5-methyl-17-(2-phenyl)ethylmorphinan-6-one hydrobromide (compound 7) as colorless crystals. A small portion of this material was recrystallized from MeOH for analyses. M.p. 94–96° C. IR (KBr): 3400 ($^+$NH), 1720 (CO) cm$^{-1}$. CI-MS: m/z 434 (M$^+$+1). $^1$H-NMR (DMSO-d$_6$) δ 10.15 (s, $^+$NH), 7.30 (m, 5 arom. H), 6.74 (d, J=8.2 Hz, 1 arom. H), 6.68 (d, J=8.2 Hz, 1 arom.), 3.87 (s, OCH$_3$—C(3)), 3.58 (s, OCH$_3$—C(14)), 1.60 (s, CH$_3$—C(5)). Analysis calculated for C$_{27}$H$_{31}$NO$_4$. HBr (514.44): C 63.04, H 6.27, N 2.72; found: C 63.18, H 6.60, N 2.39. A solution of the compound 7 (1.4 g, 3.32 mmol) in 5 ml of 48% HBr was refluxed for 30 min and then evaporated. The residue was dissolved in MeOH and again evaporated (this operation was repeated once) to afford a brownish crystalline residue (1.8 g) which was treated with hot MeOH to yield 590 mg (42%) of the compound 8.HBr. A small portion was recrystallized for analyses. M.p.>316° C. IR (KBr):3400 (⁺NH, OH), 1722 (CO)cm⁻¹. CI-MS: m/z 420 (M⁺+1). ¹H-NMR (DMSO-d₆) δ 8.95 and 8.45 (2s, ⁺NH,OH), 6.90 (m, 5 arom. H), 6.23 (dd, J=8.2, 8.2 Hz, 2 arom. H), 2.97 s, OCH3), 1.08 (s, CH₃—C(5)). Analysis calculated for C₂₆H₂₉NO₄. HBr. 0.2 MeOH (506.85): C 62.09, H 6.13, N 2.76, Br 16.77; found: C 61.79, H 6.18, N 2.63, Br 16.12.

A mixture of the compound 8. HBr (468 mg, 0.93 mmol), phenylhyrazine hydrochloride (343 mg, 2.36 nmmol), and 15 ml of glacial acetic was refluxed for 7 h. After cooling, the reaction mixture was poured on ice, alkalized with con. NH₄OH and extracted with CH₂Cl₂ (3×70 ml, 1×30 ml). The combined organic layers were washed with H₂O(3×80 ml), dried over Na₂SO₄ and evaporated. The residue (410 mg slightly brown foam) was converted into the hydrochloride salt in the usual way and crystallized from MeOH/diethyl ether to give 390 mg (83%) of the title compound 9 as slightly pink crystals. An analytic sample was obtained by recrystallization of a small portion of this material from MeOH/diethyl ether. M.p. 257–260° C. (dec.). IR (KBr): 3460 (⁺NH, NH, OH) cm⁻¹. CI-MS: m/z 493 (M⁺+1). ¹H-NMR (DMSO-d₆) δ 11.30, 9.20 and 9.05 (3 S, ⁺NH, NH, OH), 7.25 (m, 7 arom. H), 7.10 (t, J=8.2 Hz, 1 arom. H), 6.96 (t, J=8.2 Hz, 1 arom. H), 6.59 (dd, J=8.2, 8.2 Hz, 2 arom. H), 3.32 (s, OCH₃), 1.87 (s, CH₃—C(5)). Analysis calculated for C₃₂H₃₂N₂O₃. HCl. 3.7 MeOH (647.63): C 66.21, H 7.44, N 4.33; found: C 66.04, H 7.13, N 4.60.

Example 6

Synthesis of 17-(Cyclopropylmethyl)-6,7-dehydro4,5α-epoxy-3-hydroxy-14-methoxy-5-methyl-6,7-2', 3'indolomorphinan Hydrochloride (compound 10).

A mixture of 14-O-methyl-5-methylnaltrexone (H. Schmidhammer et al., Helv. Chim. Acta Vol. 77:1585–1589, 1994) (620 mg, 1.68 mmol), phenylhydrazine hydrochloride (365 mg, 2.52 mmol), and 7 ml of glacial acetic acid was refluxed for 17.5 h. After cooling, the reaction mixture was poured on ice, alkalized with NH₄OH and extracted with CH₂Cl₂ (3×70 ml, 1×20 ml). The combined organic layers were washed with H₂O(3×80 ml), dried over Na₂SO₄ and evaporated. The residue (1.11 g brown foam) was purified by column chromatography (silica gel 230–400 mesh, mobile phase CH₂Cl₂/MeOH 90:9). The corresponding fractions were combined and evaporated to afford a slightly yellow foam which was dissolved in MeOH and treated with ethereal HCl to yield 520 mg (65%) of the compound 10 as colorless crystals. For analyses a small sample was recrystallized from MeOH. M.p.>250° C. (dec.). IR (KBr):3515 and 3220 (⁺NH, NH, OH)cm⁻¹. CI-MS: m/z 443 (M⁺+1). ¹H-NMR (DMSOd₆): δ 11.30, 9.12, 8.93 (3 s,⁺NH, NH, OH), 7.34 (m, 2 arom. H), 7.09 (t, J=8.3 Hz, 1 arom. H), 6.95 (t, J=8.3 HZ, 1 arom. H), 6.63 (d, J=8.1 Hz, 1 arom. H), 6.56 (d, J=8.1 Hz, 1 arom. H), 3.24 (s, OCH₃), 1.87 (s, CH₃—C(5)). Analysis calculated for C₂₈H₃₀N₂O₃. HCl. 0.7 H₂O (491.67):C 68.41, H 6.64, N 5.70, Cl 7.21; found: C 68.52, H 6.86, N 5.65, Cl 7.48.

Example 7

Synthesis of 17-Allyl-6,7-dehydro-4,5α-epoxy-3-hydroxy-5-methyl-14-n-propyloxy-6,7-2',3'-indolomorphinan. CH₃SO₃H (compound 15).

A mixture of 7,8-dihydro-5-methyl-14-n-propyloxycodeinone described in our copending application with priority from May 18, 1994) (9; 2.67 g, 7.19 mmol), KHCO₃ (3.6 g, 35.93 mmol), 1-chloroethyl chloroformate (4.73 ml, 43.12 mmol), and 35 ml of 1,2-dichloroethane was stirred under reflux for 3.5 h. After cooling, the inorganic material was filtered off and the filtrate evaporated. The residue (4.67 g of a yellowish oil of 17-(1-chloroethoxy)-carbonyl-4,5α-epoxy-3-methoxy-5-methyl-14-n-propyloxymorphinan-6-one (compound 11); pure by TLC) was not further purified and characterized. A solution of the compound 11 in MeOH was refluxed for 1 h and then evaporated. The residue (3.54 g slightly brown foam) was crystallized from 2.5 ml MeOH/2 ml diethyl ether to give 1.68 g (66%) of 4,5α-epoxy-3-methoxy-5-methyl-14-n-propyloxy-morphinan-6-one hydrochloride (compound 12). M.p. 186–188° C. IR (KBr): 3425 (⁺NH₂), 1725 (CO)cm⁻¹. EI-MS: m/z 357 (M⁺). ¹H-NMR (DMSO-d₆): σ 10.11 and 8.15 (2 broad s, ⁺NH₂), 6.83 (d, J=8.2 Hz, 1 arom. H), 6.74 (d, J=8.2 Hz, 1 arom. H), 3.78 (s, CH₃O), 1.48 (s, CH₃—C(5)), 0.95 (t, J=7.4 Hz, CH₃). Analysis calculated for C₂₁H₂₇NO₄. HCl. 0.6 MeOH (413.14): C 62.80, H 7.42, N 3.39, Cl 8.58; found: C 62.66, H 7.34, N 3.40, Cl 8.98. A mixture of the compound 12 (1.45 g, 3.68 mmol), allyl bromide (0.36 ml, 4.06 mmol), potassium carbonate (2.9 g, 20.8 mmol), and 10 mnl of anhydrous N,N-dimethyl formamide was stirred at 80° C. (bath temperature) for 1.5 h. The inorganic solid was filtered off and the filtrate evaporated to give 1.7 g of a yellowish oily residue. This residue was partitioned between CH₂Cl₂ and H₂O. The organic layer was washed with H₂O and brine, dried over Na₂SO₄ and evaporated. The residue (1.375 g of a slightly yellow oil) was crystallized from ethanol to yield 1.28 g (88%) of 17-allyl-4,5α-epoxy-3-methoxy-5-methyl-14-n-propyloxymorphinan-6-one (compound 13) as slightly yellow crystals. M.p. 122–124° C. IR(KBr): 1720 (CO)cm⁻¹. EI-MS: m/z 397 (M⁺). ¹H-NMR (CDCl₃): δ 6.63 (d, J=8.3 Hz, 1 arom. H), 6.55 (d, J=8.3 Hz, 1 arom. H), 5.79 (m, 1 olef. H), 5.13 (m, 2 olef. H), 3.84 (s, OCH3), 1.60 (s, CH₃—C(5)), 1.00 (t, J=7.4 Hz, CH3). Analysis calculated for C₂₄H₃₁NO₄ (397.51): C 72.52, H 7.86, N 3.52; found: C 72.14, H 7.76, N 3.44. A 1 M solution of boron tribromide in CH₂Cl₂ (10.8 ml) was added to an ice-cooled solution of the compound 13 (577 mg, 1.45 mmol) in 75 ml of CH₂Cl₂ at once. After stirring at 0–5° C. for 2 h, a mixture of 20 g ice and 4 ml of conc. NH₄OH was added. The resulting mixture was stirred at room temperature for 30 min and the extracted with CH₂Cl₂ (3×50 ml). The combined organic layers were washed with brine (70 ml), dried over Na₂SO₄ and evaporated. The residue (600 mg brownish foam) was converted into the hydrobromide salt in the usual way and crystallized from MeOH to afford 314 mg (47%) of 17-allyl-4,5α-epoxy-3-hydroxy-5-methyl-14-n-propyloxymorphinan-6one hydrobromide (compound 14). M.p. 244–247° C. (dec.). IR (KBr): 3441 and 3332 (⁺NH, OH), 6.68 (d, J=8.2 Hz, 1 arom. H), 6.62 (d, J=8.2 Hz, 1 arom. H), 5.92 (m, 1 olef. H), 5.67 (m,2 olef. H), 1.49 (s, CH₃—C(5)), 0.96 (t, J=7.2 Hz, CH₃).

A mixture of the compound 14 (300 mg, 0.65 mmol), phenylhydrazine hydrochloride (187 mg, 1.29 mmol), and 30 ml of glacial acetic acid was refluxed for 7.5 h. After cooling, the reaction mixture was poured on ice, alkalized with conc. NH₄OH and extracted with CH₂Cl₂ (3×60 ml). The combined organic layers were washed with H₂O(3×80 ml) and brine (50 ml), dried over Na₂SO₄ and evaporated. The residue (325 mg brownish foam) was converted into the methane sulfonate in the usual way and recrystallized from MeOH/diethyl ether to yield 264 mg (74%) of the title compound 15. Recrystallization of a small portion of this material from ethanol afforded an analytical sample. M.p.>256° C. FABMS: m/z 457 (M⁺+1), ¹H-NMR (DMSO-d₆): δ 11.29, 9.17 and 8.45 (3 s, ⁺NH, NH, OH), 7.32 (d, J=8.2 Hz, 2 arom. H), 7.10 (t, J=8.2 Hz, 1 arom. H), 6.94 (t, J=8.2 Hz, 1 arom. H) 6.59 (s, 2 arom. H), 5.90 (m, 1 olef. H), 5.68 (m, 2 olef. H), 1.88 (s, $CH_3$—C(5)), 0,55 (t, J=7.3 Hz, $CH_3$). Analysis calculated for $C_{29}H_{32}N_2O_3H$. 0.5 $H_2O$ (561.70): C 64.15, H 66.4, N 4.99, S 5.72; found: C 64.08, H 6.87, N 5.09, S 5.87.

Example 8

Synthesis of 17-(Cyclopropylmethyl)-6,7-dehydro4,5α-epoxy-3-hydroxy-5-methyl-14-n-propyloxy-6,7-2,3'-indolomorphinan $CH_3SO_3H$ (compound 18).

A mixture of 4,5α-epoxy-3-methoxy-5-methyl-14-n-propyloxymorphinan-6-one hydrochloride (compound 12 of Example 7) (1.46 g, 3.71 mmol), potassium carbonate (2.24 g, 16.24 mmol), cyclopropylmethyl chloride (0.43 ml, 4.44 mmol), and 15 ml of anhydrous N,N-dimethyl formamide was stirred at 85° C. (bath temperature) for 36 h. The inorganic solid was filtered off and the filtrate evaporated. A solution of the residue in 30 ml of $CH_2Cl_2$ was washed with $H_2O$ (3×30 ml), dried over $Na_2SO_4$ and evaporated. The residue (1,69 g orange-yellow oil) was dissolved in diethyl ether and treated with ethereal HCl to give 920 mg (55%) of 17-(cydopropylmethyl)-4,5α-epoxy-3-methoxy-5-methyl-14-n-propyloxymorphinan-6-one hydrochloride (compound 16) as colorless powder. M.p. 156–158° C. IR (KBr): 3400 ($^+$NH), 1723 (CO) $cm^{-1}$. CI-MS: m/z 412 ($M^+$+1). $^1$H-MR (DMSO-$d_6$): δ 8.57 (s, $^+$NH), 6,85 (d, J=8.2 Hz, 1 arom. H), 6.75 (d, J=8.2 Hz, 1 rom. H), 3.79 (s, $OCH_3$), 1.51 (s, $CH_3$—C(5)), 0.97 (t, J=7.4 Hz, $CH_3$). Analysis calculated for $C_{25}H_{33}NO_4$. HCl. 0.6 $H_2O$(458.81): C 65.45, H 7.73, N 3.05, Cl 7.73; found: C 65.45, H 7.85, N 3.08, Cl 7.84.

A 1 M solution of boron tribromide in $CH_2Cl_2$ (7.3 ml) was added at once to an ice-cooled solution of the compound 16 (480 mg, 0.97 inmol) in 50 ml of $CH_2Cl_2$. After 50 min stirring at 0–5° C., a mixture of 13 g ice and 3 ml conc. $NH_4OH$ was added. The resulting mixture was stirred at room temperature for 30 min and the extracted with $CH_2Cl_2$ (3×30 ml). The combined organic layers were washed with brine (45 ml), dried over $Na_2SO_4$ and evaporated. The residue (204 mg slightly brown foam) was treated with 0.5 ml hot MeOH to afford 302 mg (55%) of 17-(cyclopropylmethyl)-4,5α-epoxy-3-hydroxy-5-methyl-14-n-propyloxymorphinan-6-one (compound 17). M.p. 184–186° C. IR (KBr): 3390 (OH), 1720 (CO)$cm^{-1}$. CI-MS: m/z 397 ($M^+$+1). $^1$H-NMR (CDCl$_3$): δ 10.24 (broad s, OH), 6.73 (d, J=8.2 Hz, 1 arom. H), 6.65 (d, J=8.2 Hz, 1 arom. H)1.62 (s, $CH_3$—C(5)), 1.00 (t,J=7.3 Hz, CH3). Analysis calculated for $C_{24}H_{31}NO_4$. 0.6 MeOH (416.74): C 70.90, H 8.08, N 3.36; found: C 70.76, H 7.73, N 3.52.

A mixture of compound 17 (230 mg, 0.58 mmol), phenylhydrazine hydrochloride (142 mg, 0.98 mmol), and 23 ml of glacial acetic acid was refluxed for 3.5 h. After cooling, the reaction mixture was poured on ice, alkalized with con. $NH_4OH$ and extracted with $CH_2Cl_2$ (3×40 ml). The combined organic layers were washed with $H_2O$ 2×50 ml) and brine (50 ml), dried and evaporated. The residue (262 mg yellow-brown foam) was converted in the usual way into the methane sulfonate and crystallized from MeOH/diethyl ether to yield 204 mg (62%) of the compound 18. M.p. 295–298 (dec.) FABMS: m/z 471 ($M^+$+1). $^1$H-NMR (DMSO-$d_6$) δ 11.27, 9.12 and 8.46 (3s, $^+$NH, NH, OH), 7.14 (m, 4 arom. H), 6.59 (s, 2 arom. H), 1.90 (s, CH3—C(5)), 0.67 (t, J=7.3 Hz, $CH_3$) Analysis calculated for $C_{30}H_{34}N_2O_3$. $CH_3SO_3H$. 1.5 $H_2O$(584.74): C 62.71, H 6.96, N 4.72, S 5.40; found: C 62.67, H 6.96, N 4.79, S 5.40.

Examples 9–24, and 28–30 illustrate further compounds, which can be prepared according to one of the methods described above.

Example 9

17-(Cyclopropylmethyl)-6,7-dehydro-4,5α-epoxy-14-hydroxy-3-(methoxymethoxy)-6,7-2',3'-benzo[b]furanomorphinan (compound 19).

M.p.129–130° C. 1H-NMR (CDCl$_3$): δ 7.45 (d, J=8.3 Hz, 1 arom. H), 7,37 (d, J=8.3 Hz, 1 arom. H), 7.25 (m, 1 arom. H), 7.16 (m, 1 arom.), 6.86 (d, J=8.3 Hz, 1 arom. H), 6.60 (d, J=8.3 Hz, 1 arom. H), 5.63 (s, H—C(5)), 5.17 and 5.06 (2 d, J=6.6, 6.6 Hz, $OCH_2O$), 3.42 (s, $CH_3O$).

Example 10

17-Cyclopropylmethyl-6,7-dehydro-4,5α-epoxy-14-hydroxy-3-(methoxymethoxy)-6,7-2',3'-(N-methoxymethylindolo)morphinan (compound 20).

$^1$H NMR (CDCl$_3$): δ 7.44 (m, 2 arom. H), 7.20 (m, 1 arom. H), 7.07 (m, 1 arom. H), 6.82 (d,j=8 Hz, 1 arom. H), 6.58 (J=8 Hz), 5.81 (s, H—C(5)), 5.79 and 5.50 (2 d, J=10.8, 10.8 Hz, $NCH_2O$), 5.12 and 5.50 (2 d, J=6.4, 6.4 Hz, $OCH_2O$), 3,41 and 3.33 (2 s, 2 $CH_3O$).

Example 11

17-(Cyclopropylmethyl)-6,7-dehydro-14-(2',6'-dichlorobenzyloxy)-4,5α-epoxy-14-3-(methoxymethoxy)-6,7-2',3'-benzo[b]furanomorphinan (compound 21).

M.p. 180–182° C. $^1$H NMR (CDCl$_3$): δ 7.41 (d, J=8.3 Hz, 1 arom. H), 7.33 (d, J=8.3 Hz, 1 arom. H), 7.23 (m, 1 arom. H) 7.14 (m, 2 arom. H), 7.03 and 7.01 (2 d, J=7.3, 7.3 Hz), 6.84 (d, J, 8.3 Hz, 1 arom. H) 6.59 (d, J=8.3 Hz, 1 arom. H), 5.56 (s, H—C(5)), 5.32 and 4.68 (2 d, J=8.7, 8.7 Hz, $OCH_2Ar$), 5.16 and 5.05 (2 d, J=6.6, 6.6 Hz, $OCH_2O$), 3.41 (s, $CH_3O$).

Example 12

17-(Cydopropylmethyl)-6,7-dehydro-14-(2',6'-dichlorobenzyloxy)-4,5α-epoxy-3-hydroxy-6,7-2',3'-benzo[b]furanomorphinan (compound 22).

M.p. 193–195° C. (dec). 1H NMR (CDCl$_3$): δ 7.42 (d, J=8.3 Hz, 1 arom. H), 7.33 (d, J=8 Hz, 1 arom. H), 7.24 (m, 1 arom. H) 7.14 (m, 2 arom. H), 7.03 and 7.01 (2 d, J=7.3 Hz, 1 arom. H), 6.64 (d, J, 8.1 Hz, 1 arom. H) 6.56 (d, J=8.1 Hz, 1 arom. H), 5.58 (s, H—C(5)), 5.32 and 4.68 (2 d, J=8.6 Hz, $OCH_2Ar$).

Example 13

17-(Cyclopropylmethyl)-6,7-dehydro-4,5α-epoxy-3 (methoxymethoxy)-14-(3'-nitrobenzyloxy)-6,7-2',3'-benzo[b]furanomorphinan (compound 23).

$^1$H NMR (CDCl$_3$): δ .25 (s, 1 arom. H), 7.28 (m, 4 arom. H), 7.15 (m, 1 arom. H) 6.87 (d, J=8.3 Hz, 1 arom. H), 6.62 (d, J=8.3 Hz, 1 arom. H), 5.66 (s, H—C(5)), 5.17 and 5.07 (2 d, J=6.6 Hz, $OCH_2O$) 4.92 and 4.44 (2 d, J=11.5 Hz, $OCH_2Ar$), 3.42 (s, $CH_3O$).

Example 14

17-(Cyclopropylmethyl)-6,7-dehydro-4,5α-epoxy-3-hydroxy-14-(3'-nitrobenzyloxy)-6,7-2',3'-benzo[b] furanomorphinan hydrochloride (compound 24).

M.p.>230° C. (dec). 1H NMR (DMCO-d6): δ 9.40 (s, OH), 9.15 (broad s, $^+$NH), 7.84 (s, 1 arom. H) 7.60 (d, J=8.8 Hz, 1 arom. H), 7.53 (d, J=7.6 Hz, 1 arom. H), 7.45 (d, J=8 Hz, 1 arom. H) 7.23 (d, J=7.6 Hz, 1 arom. H), 7.19 (d, J=7.6 Hz, 1 arom. H), 6.98 (m, 1 arom. H) 6.88 (d, J=7.6 Hz, 1 arom. H) 6.69 (d, J=8.3 Hz, 1 arom. H), 6.66 (d, J=8.3 Hz, 1 arom. H), 6.03 (s, H—C(5)), 4.98 and 4.87 (2 d, J=14, 14 Hz, $OCH_2Ph$).

Example 15

17-(Cyclopropylmethyl)-6,7-dehydro-4,5α-epoxy-3-(methoxymethoxy)-14-(2-naphtylmethoxy)-6,7-2',-3'-benzo[b]furarnorphinan (compound 25).

M.p. 198–201° C. 1H NMR (CDCl$_3$): δ 7.72–7.08 (m, 11 arom. H), 6.86 (d, J=8.3 Hz, 1 arom. H), 6.62 (d, J=8.3 Hz, 1 arom. H), 5.68 (s, H—C(5)), 5.17 and 5.07 (2 d, J=6.6, 6.6 Hz, OCH$_2$O), 5.01 and 4.57 (2 d, J=11.2, 11.2 Hz, OCH$_2$Ar), 3,42 (s, CH$_3$O).

Example 16

17-(Cydopropylmethyl)-6,7-dehydro-4,5α-epoxy-3-hydroxy-14-(2'-naphtylmethoxy)-6,7-2',3'-benzo[b]furanomorphinan hydrochloride (compound 26).

M.p.>215° C. 1H NMR (DMSO-d6): δ 9.42 (s, OH), 9.00 (broad s, $^+$NH), 7.68–6.85 (m, 11 arom. H), 6.71 (d, J=8 Hz, 1 arom. H), 6.67 (d, J=8 Hz, 1 arom. H), 6.04 (s, HC(5)), 4.92 (s, OCH$_2$Ar).

Example 17

17-(Cyclopropylmethyl)-6,7-dehydro-4,5α-epoxy-14-(2'-fluorobenzyloxy)-3-(methoxymethoxy)-6,7-2'-3'-benzo[b]furanmorphinan (compound 27).

$^1$H NMR (DMSO-d6): δ 7.56 (d, J=8 Hz, 1 arom. H), 7.49 (d, J=8 Hz, 1 arom. H), 7.31 (m, 1 arom. H), 7.21 (m, 1 arom. H), 6.81 (d, J=8.4 Hz, 1 arom. H), 6.67 (d, J=8.4 Hz), 5.72 (s, H—C(5)), 5.06 and 5.01 (2 d, J=6.4, 6.4 Hz, OCH$_2$O), 4.89 and 4.57 (2 d, J=11.6, 11.6 Hz, OCH$_2$Ar), 3,33 (s, CH$_3$O).

Example 18

17-(Cyclopropylmethyl)-6,7-dehydro-4,5α-epoxy-14-(2'-fluoro-benzyloxy)-3-hydroxy-6,7-2',3'-benzo[b]furanmorphinan Hydrochloride (compound 28).

M.p.>215° C. 1H NMR (CDCl$_3$): δ 9.45 (s, OH), 9.04 (broad s, $^+$NH), 7.54 (d, J=8.4 Hz, 1 arom. H) 7.31–6.73 (m, 7 arom. H), 6.71 (d, J=8.2 Hz, 1 arom. H), 6.66 (d, J=8.2 Hz, 1 arom. H), 5.98 (s, H—C(5)), 4.81 and 4.84 (2 d, J=12 Hz, OCH$_2$Ar).

Example 19

14-Cinnamyloxy-17-(cyclopropylmethyl)-6,7-dehydro-4,5α-epoxy-3-(methoxymethoxy)-6,7-2'-3'-benzo[b]furanomorphinan (compound 29).

M.p. 156–159° C. 1H NMR (CDCl$_3$): δ 7.47 (d, J=8 Hz, 1 arom. H), 7.33 (d, J=8 Hz, 1 arom. H), 7.28–7.07 (m, 7 arom. H), 6.84 (d, J=8.4 Hz, 1 arom. H), 6.59 (d, J=8.4 Hz, 1 arom . H), 6.38 (d, J=16 Hz, 1 olef. H), 6.13 (m, 1 olef. H), 5.68 (s, H—C(5)), 5.16 and 5.06 (2 d, J=6.4, 6.4 Hz, OCH$_2$O), 4.46 and 4.11 (2 m,OCH$_2$Ar), 3,42 (s, CH$_3$O).

Example 20

14–Cinnamyloxy-17-cyclopropylmethyl-6,7-dehydro-4,5α-epoxy-3-hydroxy-6,7-2'-3'-benzo[b]furanomorphinan Salicylate (compound 30).

$^1$H NMR (CDCl$_3$): δ 7.94 (d, J=8 Hz, 1 arom. H), 7.35 (d, J=8 Hz, 1 arom. H), 7.30–6.73 (m, 12 arom. H), 6.56 (d, J=8 Hz, 1 arom. H), 5.96 (s, 2 olef. H), 5.55 (s, HC(5)), 4.33–4.02 (m, OCH$_2$Ar).

Example 21

17-(Cyclopropylmethyl)-6,7-dehydro-4,5α-epoxy-14-methoxy-3-(methoxymethoxy)-6,7-2'-3'-benzo[b]furanomorphinan (compound 31).

$^1$H NMR (DMSO-d6): δ 7.7.56 (d, J=8 Hz, 1 arom. H), 7.52 (d, J=8 Hz, 1 arom. H), 7.32 (dd, J=8,8 Hz, 1 arom. H), 5.64 (s, H—C(5)), 5.05 and 5.00 (2 d, J=6.4, 6.4 Hz, OCH$_2$O), 3.32 (CH$_3$O).

Example 22

17-(Cyclopropylmethyl)-6,7-dehydro-4,5α-epoxy-3-hydroxy-14-methoxy-6,7-2'-3'-benzo[b]furanomorphinan hydrochloride (compound 32).

M.p.>240° C. $^1$H NMR (DMSO-d6): δ 9.47 (s, OH), 9.17 (broad s, $^+$NH), 7.61 (d, J=8 Hz, 1 arom. H), 7.53 (d, J=8 Hz, 1 arom. H), 7.36 (dd, J=8,8 Hz, 1 arom. H), 7.27 (dd, J=8,8 Hz, 1 arom. H), 6.72 (d, J=8.4 Hz, 1 arom. H), 6.65 (d, J=8.4 Hz, 1 arom. H), 5.90 (s, H—C(5)), 3.35 (s, CH$_3$O).

Example 23

17-(Cyclopropylmethyl)-14-(2'-chlorobenzyloxy)-6,7-dehydro-4,5α-epoxy-3-(methoxymethoxy)-6,7-2'-3'-(N-methoxymethylindolo)morphinan (compound 33).

$^1$H NMR (CDCl$_3$): δ 7.56 (m, 1 arom. H), 7.44 (m, 1 arom. H), 7.37–7.17 (m, 3 arom. H), 7.01 (m, 1 arom. H), 6.91 (m, 1 arom. H), 6.83 (d, J=8.2 Hz, 1 arom. H), 6.59 (dd, J=8.2, 8.2 Hz, 1 arom. H), 5.90 (s, H—C(5)), 5.82 and 5.55 (2 d, J=11.2, 11.2 Hz, NCH$_2$O), 5.13 and 5.03 (2 d, J=6.4, 6.4 Hz, OCH$_2$O), 4.98 and 4.56 (2 d, J=13, 13 Hz, OCH$_2$Ar),3.40 and 3.26 (2 s,2 CH$_3$O).

Example 24

17-(Cyclopropylmethyl)-14-(2'-chlorobenzyloxy)-6,7-dehydro-4,5α-epoxy-3-hydroxy-6,7-2'-3'-indolomorphinan hydrochloride (compound 34).

M.p.>250° C. (dec). 1H NMR (DMSO-d6): δ 11.38 (s, NH), 9.38 (s, OH), 8.76 (broad s, $^+$NH), 7.34–6.85 (m, 8 arom. H), 6.72 (d, J=8 Hz, 1 arom. H), 6.64 (d, J=8 Hz, 1 arom. H), 5.93 (s, H—C(5)), 4.80 and 4.67 (2 d, J=13, 13 Hz, OCH$_2$ Ar).

Example 25

Synthesis of 17-(Cyclopropyhnethyl)-6,7-dehydro-3,14-dimethoxy-4,5α-epoxy-6,7-2'-3'-benzo[b]furanomorphinan (compound 35).

Sodium hydride (144 mg, 6 imol; obtained from 240 mg of 60% sodium hydride dispersion in oil by washings with n-hexane) was added to a solution of naltriben methanesulfonate (P. S. Portoguese et al., J. Med. Chem., Vol. 34: 1715–1720, 1991) 500 mg, 0.97 mmol) in 10 ml of anhydrous N,N-dimethyl-formamide at 0° C. The resulting mixture was stirred at 0° C. for 15 min and then at room temperature for another 30 min. After cooling to 0° C., dimethyl sulfate (380 μl, 4 mmol) was added and stirring was continued at first at 0° C. for 30 min and then at room temperature for 3 h. Excess sodium hydride was destroyed by addition of MeOH and H$_2$O. The resulting mixture was extracted with ethyl acetate (3×40 ml), the combined organic layers were washed with H$_2$O(2×30 ml) and brine (2×30 ml), dried over Na$_2$SO$_4$ and evaporated to give a crystalline residue which was recrystallized from MeOH to afford 320 mg (74%) of compound 35. M.p. 221–224 ° C. (dec.). 1H NMR (CDCl$_3$): δ 7.47–7.14 (m, 4 arom H), 6.64 (d, J=8.4 Hz, 1 arom. H), 6.59 (d, J=8.4 Hz, 1 arom. H), 5.62 (s, H—C(5)),3.78 (s, CH$_3$O—C(3)),3.31 (s, CH$_3$O—C(14)).

Example 26

Synthesis of 17Cyclopropylmethyl-6,7-dehydro-4,5α-epoxy-14-hydroxy-6,7-2',3'-benzo[b]furanomorphinan (compound 36).

A mixture of 3-deoxynaltrexone (R. Krassnig and H. Schmidhammer, Heterocycles, Vol.38: 877–881, 1994) (1,3 g, 3.99 mmol), O-phenylhydroxylamine hydrochloride (750 mg, 5.15 mmol), methanesulfonic acid (0.75 ml, 11.55 mmol), and ethanol (30 ml) was refluxed for 20 h. After cooling, the mixture was diluted with $H_2O$, alkalized with conc. $NH_4OH$ and extracted with $CH_2Cl_2$ (4×40 ml). The combined organic layers were washed with $H_2O$ (2×30 ml) and brine (30 ml), dried over $Na_2SO_4$ and evaporated to give a brownish oil which was crystallized form MeOH to yield 1.1 mg (69%) of compound 36. M.p.>260° C. $^1H$ NMR ($CDCl_3$): δ 7.45 (d, J=8 Hz, 1 arom. H), 7.37 (d, J=8 Hz, 1 arom. H), 7.26–7.13 (m, 2 arom. H), 7.01 (dd,=7.8, 7.8 Hz, 1 arom. H), 6.67 (d, J=7.8 Hz, 1 arom. H), 6.59 (d, J=7.8 Hz, 1 arom. H), 5.59 (s, H—C(5)),5.00 (broad s, OH).

Example 27

Synthesis of 17-(Cyclopropylmethyl)-6,7-dehydro-4,5α-epoxy-14-hydroxy-6,7-2'-3'-indolomorphinan hydrochloride (compound 37).

A mixture of 3-deoxynaltrexone (R. Krassnig and H. Schmidhammer, Heterocydes, Vol. 38: 877–881, 1994) (1,5 g, 4.6 mmol), phenylhydrazine hydrochloride (1.0 mg, 6.9 mmol), 1M HCl in ether (5 ml), and methanol (20 ml) was stirred at room temperature for 3 days. After concentration to ca. half of the original volume in vacuo, the solution was refrigerated overnight. The colorless crystals formed were collected to yield 1.54 g (77%) of compound 37. M.p.>240° C. (dec.). 1H NMR (DMSO-d6): δ 11.37 (s, NH), 9.01 (broad s, $^+$NH), 7.36–6.94 (m, 5 arom. H), 6.78 (d, J=7.8 Hz, 1 arom. H), 6.59 (d, J=7.8 Hz, 1 arom. H), 6.55 (s, OH).

Example 28

17(Cyclopropylmethyl)-6,7-dehydro-4,5α-epoxy-3-hydroxy-14-(3'-chlorobenzyloxy)-6,7,2',3'-benzo[b]furanomorphinan, hydrochloride (compound 39).

$^1H$ NMR (DMSO-d6): δ 9.40 (s, OH), 8.59 (broad s, +NH), 7.53–6.90 (m, 8 arom. H), 6.65 (s, 2 arom. H), 6.03 (s, H—C(5)),4.74 and 4.62 (2 d, J=13.6, 13.6 Hz, $OCH_2$(3'-ClPh)). Analysis calculated for $C_{33}H_{30}ClNO_4$. HCl. 1.5 $H_2O$: C 65.67, H 5.68, N 2.32; found: C 65.31, H 5.37, N 2.33.

Example 29

17-(Cyclopropylmethyl)-6,7-dehydro-4,5α-epoxy-3-hydroxy-14-(2'chlorobenzyloxy)-6,7,2',3'-benzo[b]furanomorphinan Hydrochloride (compound 41).

M.p.>220° C. $^1H$ NMR (DMSO-d6): δ 9.40 (s, OH), 8.59 (broad s, +NH), 7.56–6.90 (m, 8 arom. H), 6.66 (m, 2 arom. H), 6.03 (s, H—C(5)), 4.74 (s, OCH2(2-ClPh)). Analysis calculated for $C_{33}H_{30}ClNO_4$. Hcl.1.5 $H_2O$: C 65.67, H 5.68, N, 2.32. Found: C 65.72, H 5.48, N 2.25.

Example 30

14-Allyloxy-17-(cyclopropylmethyl)-6,7-dehydro-4,5α-epoxy-3-hydroxy-1'-allyl-6,7-2',3'-indolomorphinan hydrochloride (compound 42).

NMR of the free base (colorless oil) $^1H$ NMR ($CDCl_3$): δ 7.40 (d, J=8.4 Hz, 1 arom. H), 7.24 (m, 1 arom. H), 7.15 (m, 1 arom. H), 7.03 (m, 1 arom. H), 6.57 (d, J=8.4 Hz, 1 arom. H), 6.50 (d, J=8.4 Hz, 1 arom. H), 6.08 (m, 1 olef. H), 5.76 (m, 1 olef. H), 5.72 (s, H—C(5)), 5.15–4.75 (m, 6 H, $CH_2N$,2 $CH_2$=C), 4.24 and 3.92 (2 dd, J=12.4, 4.8 Hz, $CH_2O$). This free base was dissolved in ethyl ether and treated with HCl/ether solution HCl at 0° C. Isolation of the precipitate provided the title compound 42 as a solid.

Pharmaceutical Preparations

For the preparation of a pharmaceutical formulation, the active ingredient may be formulated to an injection, capsule, tablet, suppository, solution or the like. Oral formulation and injection are preferably employed. The pharmaceutical formulation may comprise the &selective antagonist alone or may also comprise expedients such as stabilizers, buffering agents, diluents, isotonic agents, antiseptics and the like. The pharmaceutical formulation may contain the above described active ingredient in the amount of 1–95% by weight, preferably 10–60% by weight. The dose of the active ingredient may be appropriately selected depending on the objects of administration, administration route and conditions of the patients. The active ingredient may be administered in doses between 1 mg and 1 g per day in case of administration by injection and in doses between 10 mg and 5 g per day in case of oral administration. The preferred dose for injection is 20–500 mg per day.

Biological Studies

δ-Antagonism was assessed using the electrical stimulated guinea-pig ileum longitudinal muscle preparation (GPI; containing μ and κ opioid receptors) and mouse vas deferens preparation (MVD; containing μ, κ and δ opioid receptors) (H. Schmidhammer et al., J. Med. Chem., Vol. 32: 418–421, 1989; H Schnmidhammer et al., J. Med. Chem., Vol. 33:1200–1206,1990). The activity of the compound 1 of the Examples for inhibiting the suppression of contraction of the organs by three receptor selective agonists (DAMGO, μ; Cl 977, κ; DPDPE, δ) was measured. The compound exhibited δ-selective opioid antagonism with very good μ/δ and κ/δ selectivity ratios.

Conclusion

The pharmacological studies of the novel morphinan derivatives of formula (I) of the present invention have shown that these compounds have selectivity for δ opioid receptors and are effective as opioid antagonists.

I claim:

1. A compound according to formula (I)

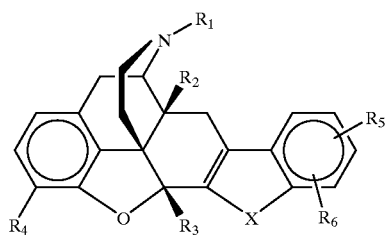

(I)

wherein $R_1$ represents $C_2$–$C_{10}$ alkenyl; $C_4$–$C_{10}$ cycloalkylalkyl wherein the cycloalkyl is $C_3$–$C_6$ cycloalkyl and the alkyl is $C_1$–$C_4$ alkyl; $C_4$–$C_{10}$ cykloalkenylalkyl wherein the cycloalkenyl is $C_3$–$C_6$ cykloalkenyl and the alkyl is $C_1$–$C_4$ alkyl; $C_7$–$C_{16}$ arylalkyl wherein the aryl is $C_6$–$C_{10}$ aryl and the alkyl is $C_1$–$C_6$ alkyl; $C_8$–$C_{16}$ arylalkenyl wherein the aryl is $C_6$–$C_{10}$ aryl and the alkenyl is $C_2$–$C_6$ alkenyl;

$R_2$ represents hydrogen, hydroxy, $C_1$–$C_6$ alkoxy; $C_2$–$C_6$ alkenyloxy; $C_7$–$C_{16}$ arylakyloxy wherein the aryl is $C_6$–$C_{10}$ aryl and the alkyloxy is $C_1$–$C_6$ alkyloxy; $C_7$–$C_{16}$ arylalkenyloxy wherein the aryl is $C_6$–$C_{10}$ aryl and the alkenyloxy is $C_2$–$C_6$ alkenyloxy; $C_1$–$C_6$ alkanoyloxy; $C_7$–$C_{16}$ arylalkanoyloxy wherein the aryl is $C_6$–$C_{10}$ aryl and the alkanoyloxy is $C_1$–$C_6$ alkanoyloxy;

$R_3$ represents hydrogen, $C_1$–$C_6$ alkyl; $C_2$–$C_6$ alkenyl; $C_7$–$C_{16}$ arylalkyl wherein the aryl is $C_6$–$C_{10}$ aryl and the alkyl is $C_1$–$C_6$ alkyl; $C_7$–$C_{16}$ arylalkenyl wherein the aryl is $C_6$–$C_{10}$ aryl and the alkenyl is $C_2$–$C_6$ alkenyl; hydroxy($C_1$–$C_6$)alkyl; alkoxyalkyl wherein the alkoxy is $C_1$–$C_6$ alkoxy and the alkyl is $C_1$–$C_6$ alkyl; $CO_2H$; $CO_2$($C_1$–$C_6$ alkyl);

$R_4$ is hydrogen; hydroxy; $C_1$–$C_6$ alkoxy; $C_7$–$C_{16}$ arylalkyloxy wherein the aryl is $C_6$–$C_{10}$ aryl and the alkyloxy is $C_1$–$C_6$ akyloxy; $C_2$–$C_6$ alkenyloxy; $C_1$–$C_6$ alkanoyloxy; $C_7$–$C_{16}$ arylalkanoyloxy wherein the aryl is $C_6$–$C_{10}$ aryl and the alkanoyloxy is $C_1$–$C_6$ alkanoyloxy; $C_2$–$C_{10}$ alkyloxyalkoxy wherein alkyloxy is $C_1$–$C_4$ alkyloxy and alkoxy is $C_1$–$C_6$ alkoxy;

$R_5$ and $R_6$ each independently represent hydrogen; OH; $C_1$–$C_6$ alkoxy; $C_1$–$C_6$ alkyl; hydroxyalkyl wherein the alkyl is $C_1$–$C_6$ alkyl; halo; nitro; cyano; SCN trifluoromethyl; $CO_2H$; $CO_2$($C_1$–$C_6$ alkyl); $CONH_2$; CONH ($C_1$–$C_6$ alkyl); CON($C_1$–$C_6$ alkyl)$_2$; amino; $C_1$–$C_6$ monoalkyl amino; $C_1$–$C_6$ dialkyl amino; $C_5$–$C_6$ cycloalkyl amino; SH; $SO_3H$; $SO_3$($C_1$–$C_6$ alkyl); $SO_2$ ($C_1$–$C_6$ alkyl); $SO_2NH_2$; $SO_2NH$($C_1$–$C_6$ alkyl); $SO_2NH$ ($C_7$–$C_{20}$ arylalkyl); $SO(C_1^{14}$ $^{C}_6$ alkyl); or $R_5$ and $R_6$ together form a phenyl ring which may be unsubstituted or substituted by halo, nitro, cyano, thiocyanato; $C_1$–$C_6$ alkyl; trifluoromethyl; $C_1$–$C_6$ alkoxy, $CO_2H$, $CO(C_1$–$C_6$ alkyl), amino, $C_1$–$C_6$ monoalkylamino, $C_1$–$C_6$ dialkylamino, SH; $SO_3H$; H; $SO_3$($C_1$–$C_6$ alkyl), $SO_2$($C_1$–$C_6$ alkyl), $SO(C_1$–$C_6$ alkyl), and X represents oxygen; sulfur; CH=CH or $NR_9$ wherein $R_9$ is H, $C_1$–$C_6$ alkyl, $C_2$–$C_6$ alkenyl, $C_7$–$C_{16}$ arylalkyl wherein the aryl is $C_6$–$C_{10}$ aryl and the alkyl is $C_1$–$C_6$ alkyl, $C_7$–$C_{16}$ arylkenyl wherein the aryl is $C_6$–$C_{10}$ aryl and the alkenyl is $C_2$–$C_6$ alkenyl; $C_1$–$C_6$ alkanoyl;

and wherein
   aryl is unsubstituted or mono- or di- or trisubstituted independently with hydroxy, halo, nitro, cyano, SCN trifluoromethyl, $C_1$–$C_3$ alkyl, $C_1$–$C_3$ alkoxy, $CO_2H$, $CO_2$ ($C_1$–$C_3$)alkyl, $CONH_2$, CONH($C_1$–$C_3$ alkyl), CON($C_1$–$C_3$ alkyl), CO($C_1$–$C_3$ alkyl), amino, ($C_1$–$C_3$ monoalkyl)amino, ($C_1$–$C_3$ dialkyl)amino, $C_5$–$C_6$ cycloalkylamino ($C_1$–$C_3$ alkanoyl)amino, SH, $SO_3H$, $SO_3$ ($C_1$–$C_3$ alkyl), $SO_2$ ($C_1$–$C_3$ alkyl), $SO(C_1$–$C_3$ alkyl), $C_1$–$C_3$ alkylthio or $C_1$–$C_3$ alkanoylthio; and
   with the following provisos:
      (i) when $R_2$ is hydroxy, $R_3$ is not hydrogen unless $R_4$ is hydrogen, $OCH_2OCH3$, $OCH_2OC_2H_5$ or $OC(Ph)_3$; or
      (ii) $R_3$ is not hydrogen unless $R_4$ is $C_2$–$C_{10}$ alkyloxyalkoxy, or $R_2$ is $C_7$–$C_{16}$ arylalkenyloxy or $C_2$–$C_6$ alkenyloxy;

or a pharmaceutically acceptable salt thereof.

2. A compound according to claim 1, wherein:
   $R_1$ is selected from allyl, cinnamyl, cyclopropylmethyl or cyclobutylmethyl;
   $R_2$ is methoxy, ethoxy, n-propyloxy, benzyloxy, benzyloxy substituted in the aromatic ring with F, Cl, $NO_2$, CN, $CF_3$, $CH_3$ or $OCH_3$; allyloxy, cinnamyloxy or 3-phenylpropyloxy;

$R_3$ is hydrogen, methyl, ethyl, benzyl or allyl;
   $R_4$ is hydroxy, methoxy, methoxymethoxy or acetyloxy;
   $R_5$ and $R_6$ are each and independently hydrogen; nitro; cyano; chloro, fluoro, bromo, trifluoromethyl; $CO_2H$; $CO_2$; $CH_3$; $CONH_2$; $CONHCH_3$; SH; $SO_2NH_2$; $N(CH_3)_2$; or $SO_2CH_3$;
   X is oxygen; NH or $NCH_3$, N-benzyl, or N-allyl.

3. A compound according to claim 1, in the form of a pharmaceutically acceptable salt.

4. A compound according to claim 3, wherein said salt is an inorganic salt.

5. A compound according to claim 3, wherein said salt is an organic salt.

6. A compound selected from the group consisting of:

17-(cyclopropylmethyl)-6,7-dehydro-4,5α-epoxy-14-ethoxy-3-hydroxy-5-methyl-6,7-2',3'-indolomorphinan×HCl;

17-allyl-6,7-dehydro-4,5α-epoxy-14-ethoxy-3-hydroxy-5-methyl-6,7-2',3'-indolomorphinan×HCl;

6,7-dehydro-4,5α-epoxy-14-ethoxy-3-hydroxy-5-methyl-17-(2-phenyl)ethyl-6,7-2',3'-indolomorphinan× HCl;

17-allyl-6,7-dehydro-4,5α-epoxy-3-hydroxy-14-methoxy-5-methyl-6,7-2',3'-indolomorphinan×HCl;

6,7-dehydro-4,5α-epoxy-3-hydroxy-14-methoxy-5-methyl-17-(2-phenyl)ethyl-6,7-2',3'-indolomorphinan× HCl;

17-(cyclopropylmethyl)-6,7-dehydro-4,5α-epoxy-3-hydroxy-14-methoxy-5-methyl-6,7-2',3'-indolomorphinan×HCl;

17-allyl-6,7-dehydro-4,5α-epoxy-3-hydroxy-5-methyl-14-n-propyloxy-6,7-2',3'-indolomorphinan× $CH_3SO_3H$;

17-(cyclopropylmethyl)-6,7-dehydro-4,5α-epoxy-3-hydroxy-5-methyl-14-n-propyloxy-6,7-2',3'-indolomorphinan×$CH_3SO_3H$;

17-(cyclopropylmethyl)-6,7-dehydro-4,5α-epoxy-14-hydroxy-3-(methoxymethoxy)-6,7-2',3'-benzo[b]furanomorphinan;

17-(cyclopropylmethyl)-6,7-dehydro-4,5α-epoxy-14-hydroxy-3-(methoxymethoxy)-6,7-2',3'-(N-methoxymethylindolo)morphinan;

17-(cyclopropylmethyl)-6,7-dehydro-14-(2',6'-dichlorobenzyloxy)-4,5α-epoxy-3-(methoxymethoxy)-6,7-2',3'-benzo[b]furanomorphinan;

17-(cyclopropylmethyl)-6,7-dehydro-14-(2',6'-dichlorobenzyloxy)-4,5α-epoxy-3-hydroxy-6,7-2',3'-benzo[b]furanomorphinan;

17-(cyclopropylmethyl)-6,7-dehydro-4,5α-epoxy-3-(methoxymethoxy)-14-(3'-nitrobenzyloxy)-6,7-2',3'-benzo[b]furanomorphinan;

17-(cyclopropylmethyl)-6,7-dehydro-4,5α-epoxy-3-hydroxy-14-(3'-nitrobenzyloxy)-6,7-2',3'-benzo[b]furanomorphinan×HCl;

17-(cyclopropylmethyl)-6,7-dehydro-4,5α-epoxy-3-(methoxymethoxy)-14-(2'-naphthylmethoxy)-6,7-2',3'-benzo[b]furanomorphinan;

17-(cyclopropylmethyl)-6,7-dehydro-4,5α-epoxy-3-hydroxy-14-(2'-naphtylmethoxy)-6,7-2',3'-benzo[b]furanomorphinan×HCl;

17-(cyclopropylmethyl)-6,7-dehydro-4,5α-epoxy-14-(2'-flurobenzyloxy)-3-(methoxymethoxy)-6,7-2',3'-benzo[b]furanomorphinan;

17-(cyclopropylmethyl)-6,7-dehydro-4,5α-epoxy-14-(2'-flurobenzyloxy)-3-hydroxy-6,7-2',3'-benzo[b]furanomorphinan×HCl;

14-cinnamyloxy-17-(cyclopropylmethyl)-6,7-dehydro-4,5α-epoxy-3-(methoxymethoxy)-6,7-2',3'-benzo[b]furanomorphinan;

14-cinnamyloxy-17-(cyclopropylmethyl)-6,7-dehydro-4,5α-epoxy-3-hydroxy-6,7-2',3'-benzo[b]furanomorphinan salicylate;

17-(cyclopropylmethyl)-6,7-dehydro-4,5α-epoxy-14-methoxy-3-(methoxymethoxy)-6,7-2',3'-benzo[b]furanomorphinan;

17-(cyclopropylmethyl)-14-(2'-chlorobenzyloxy)-6,7-dehydro-4,5α-epoxy-3-(methoxymethoxy)-6,7-2',3'-(N-methoxymethylindolo)morphinan;

17-(cyclopropylmethyl)-14-(2'-chlorobenzyloxy)-6,7-dehydro-4,5α-epoxy-3-hydroxy-6,7-2',3'-indolomorphinan×HCl;

17-(cyclopropylmethyl)-6,7-dehydro-4,5α-epoxy-14-hydroxy-6,7-2',3'-benzo[b]furanomorphinan;

17-(cyclopropylmethyl)-6,7-dehydro-4,5α-epoxy-14-hydroxy-6,7-2',3'-indolomorphinan×HCl;

17-(cyclopropylmethyl)-6,7-dehydro-4,5α-epoxy-3-hydroxy-14-(3'-chlorobenzyloxy)-6,7-2',3'-benzo[b]furanomorphinan×HCl;

17-(cyclopropylmethyl)-6,7-dehydro-4,5α-epoxy-3-hydroxy-14-(2'-chlorobenzyloxy)-6,7-2',3'-benzo[b]furanomorphinan×HCl; and 14-allyloxy-17-(cyclopropylmethyl)-6,7-dehydro-4,5α-epoxy-3-hydroxy-1'-allyl-6,7-2',3'-indolomorphinan×HCl.

7. A compound selected from the group consisting of:

17-(cyclopropylmethyl)-6,7-dehydro-4,5α-epoxy-14-ethoxy-3-hydroxy-5-methyl-6,7-2',3'-indolomorphinan hydrochloride;

17-(cyclopropylmethyl)-6,7-dehydro-4,5α-epoxy-3-hydroxy-14-methoxy-5-methyl-6,7-2',3'indolomorphinan hydrochloride;

17-(cyclopropylmethyl)-6,7-dehydro-4,5α-epoxy-3-hydroxy-5-methyl-14-n-propyloxy-6,7-2',3'-indolomorphinan CH$_3$SO$_3$H;

17-(cyclopropylmethyl)-6,7-dehydro-14-(2',6'-dichlorobenzyloxy)-4,5α-epoxy-3-hydroxy-6,7-2',3'-benzo[b]furanomorphinan;

17-(cyclopropylmethyl)-6,7-dehydro-4,5α-epoxy-3-hydroxy-14-(3'-nitrobenzyloxy)-6,7-2',3'-benzo[b]furanomorphinan hydrochloride;

17-(cyclopropylmethyl)-6,7-dehydro-4,5α-epoxy-3-hydroxy-14-(2'-naphtylmethoxy)-6,7-2',3'-benzo[b]furanomorphinan hydrochloride;

17-(cyclopropylmethyl)-6,7-dehydro-4,5α-epoxy-14-(2'-fluoro benzyloxy)-3'-hydroxy-6,7-2',3'-benzo[b]furanomorphinan hydrochloride;

14-cinnamyloxy-17-(cyclopropylmethyl)-6,7-dehydro-4,5α-epoxy-3-hydroxy-6,7-2'-3'-benzo[b]furanomorphinan salicylate;

17-(cyclopropylmethyl)-14-(2'-chlorobenzyloxy)-6,7-dehydro-4,5α-epoxy-3-hydroxy-6,7-2'-3'-indolomorphinan hydrochloride;

17-cyclopropylmethyl-6,7-dehydro-4,5α-epoxy-14-hydroxy-6,7-2',3'-benzo [b]furanomorphinan;

17-(cyclopropylmethyl)-6,7-dehydro-4,5α-epoxy-14-hydroxy-6,7-2'-3'-indolomorphinan hydrochloride;

17(cyclopropylmethyl)-6,7-dehydro-4,5α-epoxy-3-hydroxy-14-(3'-chlorobenzyloxy)-6,7,2',3'-benzo[b]furanomorphinan hydrochloride;

17-(cyclopropylmethyl)-6,7-dehydro-4,5α-epoxy-3-hydroxy-14-(2'-chlorobenzyloxy)-6,7,2',3'-benzo[b]furanomorphinan hydrochloride; and 14-allyloxy-17-(cyclopropylmethyl)-6,7-dehydro-4,5α-epoxy-3-hydroxy-1'-allyl-6,7-2',3'-indolomorphinan hydrochloride.

8. A method for suppressing the rejection of transplants in a subject after organ transplantation comprising administering an effective amount of a compound according to claim 1 to said subject.

9. A method for the treatment of a subject suffering from a rheumatic disease, comprising administering an effective amount of a compound according to claim 1 to said subject.

10. A method according to claim 9, wherein the rheumatic disease is rheumatoid arthritis.

11. A pharmaceutical composition comprising a compound or a pharmaceutically acceptable salt thereof according to claim 1 as an active ingredient together with a pharmaceutically acceptable carrier.

* * * * *